United States Patent
Meridew et al.

(10) Patent No.: US 8,021,432 B2
(45) Date of Patent: Sep. 20, 2011

(54) APPARATUS FOR USE OF POROUS IMPLANTS

(75) Inventors: Jason D Meridew, Syracuse, IN (US); Adolph Lombardi, New Albany, OH (US); Keith Berend, New Albany, OH (US); Troy Hershberger, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1364 days.

(21) Appl. No.: 11/546,500

(22) Filed: Oct. 11, 2006

(65) Prior Publication Data
US 2007/0129809 A1    Jun. 7, 2007

Related U.S. Application Data

(63) Continuation-in-part of application No. 11/357,868, filed on Feb. 17, 2006, now Pat. No. 7,597,715.

(51) Int. Cl.
*A61F 2/32* (2006.01)
(52) U.S. Cl. ............ 623/22.32; 623/22.36; 623/22.37
(58) Field of Classification Search .... 623/22.21–22.31, 623/22.39, 22.38
See application file for complete search history.

(56) References Cited

U.S. PATENT DOCUMENTS

| | | | |
|---|---|---|---|
| 3,353,259 A | 11/1967 | Kirkpatrick | |
| 3,605,123 A | 9/1971 | Hahn | |
| 3,677,795 A | 7/1972 | Bokros et al. | |
| 3,808,606 A | 5/1974 | Tronzo | |
| 3,840,904 A | 10/1974 | Tronzo | |
| 3,855,638 A | 12/1974 | Pilliar | |
| 3,896,500 A | 7/1975 | Rambert et al. | |
| 3,905,777 A | 9/1975 | Lacroix | |
| 3,906,550 A | 9/1975 | Rostoker et al. | |
| 3,938,499 A | 2/1976 | Bucalo | |

(Continued)

FOREIGN PATENT DOCUMENTS

DE    24 04 214 C3    1/1974

(Continued)

OTHER PUBLICATIONS

International Search Report and Written Opinion for PCT/US2008/002372 mailed Dec. 9, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

(Continued)

*Primary Examiner* — David H Willse
*Assistant Examiner* — Javier G Blanco
(74) *Attorney, Agent, or Firm* — Harness, Dickey

(57) ABSTRACT

An acetabular cup assembly implantable at an acetabular socket can include an acetabular cup defining a partially spherical bone engaging surface and having a uniform thickness. A spacer can include a body portion formed of porous metal and define a radial support surface. The porous metal can be adapted to receive bone ingrowth through interstitial space at pores defined therein. The spacer can further comprise a piercing portion adapted to be advanced into the acetabular socket. The spacer can bridge a gap defined between the acetabular socket and the acetabular cup. Filler can be disposed between the acetabular cup and the acetabular socket in areas adjacent to the spacer such that the spacer and the filler collectively define a continuous support surface adapted to support the acetabular cup at the bone engaging surface.

20 Claims, 12 Drawing Sheets

U.S. PATENT DOCUMENTS

| | | |
|---|---|---|
| 3,986,212 A | 10/1976 | Sauer |
| 4,051,559 A | 10/1977 | Pifferi |
| 4,164,794 A | 8/1979 | Spector et al. |
| 4,168,326 A | 9/1979 | Broemer et al. |
| 4,184,213 A | 1/1980 | Heimke |
| 4,187,559 A | 2/1980 | Grell et al. |
| 4,205,400 A | 6/1980 | Shen et al. |
| 4,206,271 A | 6/1980 | Norling et al. |
| 4,217,666 A | 8/1980 | Averill |
| 4,224,698 A | 9/1980 | Hopson |
| 4,234,972 A | 11/1980 | Hench et al. |
| 4,285,070 A | 8/1981 | Averill |
| 4,285,071 A | 8/1981 | Nelson et al. |
| 4,307,472 A | 12/1981 | Morris |
| 4,309,488 A | 1/1982 | Heide et al. |
| 4,330,891 A | 5/1982 | Brånemark et al. |
| 4,345,339 A | 8/1982 | Müller et al. |
| 4,351,069 A | 9/1982 | Ballintyn et al. |
| 4,355,428 A | 10/1982 | Deloison et al. |
| 4,362,681 A | 12/1982 | Spector et al. |
| 4,479,271 A | 10/1984 | Bolesky et al. |
| 4,542,539 A | 9/1985 | Rowe, Jr. et al. |
| 4,563,778 A | 1/1986 | Roche et al. |
| 4,566,138 A | 1/1986 | Lewis et al. |
| 4,570,271 A | 2/1986 | Sump |
| 4,612,160 A | 9/1986 | Donlevy et al. |
| 4,636,219 A | 1/1987 | Pratt et al. |
| 4,644,942 A | 2/1987 | Sump |
| 4,659,331 A | 4/1987 | Matthews et al. |
| 4,666,450 A | 5/1987 | Kenna |
| 4,685,923 A | 8/1987 | Mathys |
| 4,693,721 A | 9/1987 | Ducheyne |
| 4,715,859 A | 12/1987 | Schelhas et al. |
| 4,715,860 A | 12/1987 | Amstutz et al. |
| 4,743,256 A | 5/1988 | Brantigan |
| 4,743,262 A | 5/1988 | Tronzo |
| 4,756,862 A | 7/1988 | Spector et al. |
| 4,769,041 A | 9/1988 | Morscher |
| 4,778,473 A | 10/1988 | Matthews et al. |
| 4,778,474 A | 10/1988 | Homsy |
| 4,795,469 A | 1/1989 | Oh |
| 4,801,301 A | 1/1989 | Noiles |
| 4,813,959 A | 3/1989 | Cremascoli |
| 4,828,565 A * | 5/1989 | Duthoit et al. ............... 623/22.3 |
| 4,840,632 A | 6/1989 | Kampner |
| 4,842,606 A | 6/1989 | Kranz et al. |
| 4,851,006 A | 7/1989 | Tuke |
| 4,854,496 A | 8/1989 | Bugle |
| 4,863,474 A | 9/1989 | Brown et al. |
| 4,863,475 A | 9/1989 | Andersen et al. |
| 4,863,538 A | 9/1989 | Deckard |
| 4,871,368 A | 10/1989 | Wagner |
| 4,883,490 A | 11/1989 | Oh |
| 4,883,491 A | 11/1989 | Mallory et al. |
| 4,892,549 A | 1/1990 | Figgie, III et al. |
| 4,904,265 A | 2/1990 | MacCollum et al. |
| 4,919,675 A | 4/1990 | Dietschi et al. |
| 4,923,473 A | 5/1990 | Griss et al. |
| 4,936,847 A | 6/1990 | Manginelli |
| 4,936,856 A | 6/1990 | Keller |
| 4,936,861 A | 6/1990 | Muller et al. |
| 4,944,759 A | 7/1990 | Mallory et al. |
| 4,950,270 A | 8/1990 | Bowman et al. |
| 4,950,299 A | 8/1990 | Noiles |
| 4,955,919 A | 9/1990 | Pappas et al. |
| 4,957,819 A | 9/1990 | Kawahara et al. |
| 4,963,154 A | 10/1990 | Anapliotis et al. |
| 4,969,907 A | 11/1990 | Koch et al. |
| 4,969,910 A | 11/1990 | Frey et al. |
| 4,976,738 A | 12/1990 | Frey et al. |
| 4,978,355 A | 12/1990 | Frey et al. |
| 4,978,356 A | 12/1990 | Noiles |
| 4,978,358 A | 12/1990 | Bobyn |
| 4,997,445 A | 3/1991 | Hodorek |
| 5,004,476 A | 4/1991 | Cook |
| 5,009,665 A | 4/1991 | Serbousek et al. |
| 5,013,324 A | 5/1991 | Zolman et al. |
| 5,018,285 A | 5/1991 | Zolman et al. |
| 5,019,105 A | 5/1991 | Wiley |
| 5,021,062 A | 6/1991 | Adrey et al. |
| 5,021,063 A | 6/1991 | Täger |
| 5,024,670 A | 6/1991 | Smith et al. |
| 5,027,998 A | 7/1991 | Bugle |
| 5,030,233 A | 7/1991 | Ducheyne |
| 5,047,182 A | 9/1991 | Sundback et al. |
| 5,080,672 A | 1/1992 | Bellis |
| 5,080,674 A | 1/1992 | Jacobs et al. |
| 5,080,685 A | 1/1992 | Bolesky et al. |
| 5,084,051 A | 1/1992 | Tormala et al. |
| 5,092,897 A | 3/1992 | Forte |
| 5,096,518 A | 3/1992 | Fujikawa et al. |
| 5,098,435 A | 3/1992 | Stednitz et al. |
| 5,104,410 A | 4/1992 | Chowdhary |
| 5,108,432 A | 4/1992 | Gustavson |
| 5,133,764 A | 7/1992 | Pappas et al. |
| 5,152,796 A | 10/1992 | Slamin |
| 5,152,797 A | 10/1992 | Luckman et al. |
| 5,156,626 A | 10/1992 | Broderick et al. |
| 5,163,961 A | 11/1992 | Harwin |
| 5,167,502 A | 12/1992 | Kawahara et al. |
| 5,176,711 A | 1/1993 | Grimes |
| 5,181,928 A | 1/1993 | Bolesky et al. |
| 5,192,329 A | 3/1993 | Christie et al. |
| 5,198,308 A | 3/1993 | Shetty et al. |
| 5,201,766 A | 4/1993 | Georgette |
| 5,203,787 A | 4/1993 | Noblitt et al. |
| 5,211,665 A | 5/1993 | Ku |
| 5,226,915 A | 7/1993 | Bertin |
| 5,236,457 A | 8/1993 | Devanathan |
| 5,236,462 A | 8/1993 | Mikhail |
| 5,246,530 A | 9/1993 | Bugle et al. |
| 5,282,861 A | 2/1994 | Kaplan |
| 5,286,260 A | 2/1994 | Bolesky et al. |
| 5,290,315 A | 3/1994 | DeCarlo, Jr. |
| 5,310,408 A | 5/1994 | Schryver et al. |
| 5,314,490 A | 5/1994 | Wagner et al. |
| 5,323,954 A | 6/1994 | Shetty et al. |
| 5,326,367 A | 7/1994 | Robioneck et al. |
| 5,326,368 A | 7/1994 | Collazo |
| 5,343,877 A | 9/1994 | Park |
| 5,348,788 A | 9/1994 | White |
| 5,358,532 A | 10/1994 | Evans et al. |
| 5,360,448 A | 11/1994 | Thramann |
| 5,360,452 A | 11/1994 | Engelhardt et al. |
| 5,370,692 A | 12/1994 | Fink et al. |
| 5,370,698 A | 12/1994 | Heimke et al. |
| 5,370,702 A | 12/1994 | Jones |
| 5,370,704 A | 12/1994 | DeCarlo, Jr. |
| 5,370,706 A | 12/1994 | Bolesky et al. |
| 5,376,122 A | 12/1994 | Pappas et al. |
| 5,380,325 A | 1/1995 | Lahille et al. |
| 5,397,359 A | 3/1995 | Mittelmeier et al. |
| 5,405,389 A | 4/1995 | Conta et al. |
| 5,415,704 A | 5/1995 | Davidson |
| 5,443,510 A | 8/1995 | Shetty et al. |
| 5,443,512 A | 8/1995 | Parr et al. |
| 5,443,519 A | 8/1995 | Averill et al. |
| 5,484,539 A | 1/1996 | Tersi et al. |
| 5,486,181 A | 1/1996 | Cohen et al. |
| 5,496,372 A | 3/1996 | Hamamoto et al. |
| 5,504,300 A | 4/1996 | Devanathan et al. |
| 5,505,984 A | 4/1996 | England et al. |
| 5,507,824 A | 4/1996 | Lennox |
| 5,509,933 A | 4/1996 | Davidson et al. |
| 5,534,027 A | 7/1996 | Hodorek |
| 5,535,810 A | 7/1996 | Compton et al. |
| 5,540,713 A | 7/1996 | Schnepp-Pesch et al. |
| 5,545,227 A | 8/1996 | Davidson et al. |
| 5,549,685 A | 8/1996 | Hayes |
| 5,549,691 A | 8/1996 | Harwin |
| 5,549,698 A | 8/1996 | Averill et al. |
| 5,549,701 A | 8/1996 | Mikhail |
| 5,571,187 A | 11/1996 | Devanathan |
| 5,571,194 A | 11/1996 | Gabriel |
| 5,571,198 A | 11/1996 | Drucker et al. |
| 5,571,200 A | 11/1996 | Cohen et al. |
| 5,571,201 A | 11/1996 | Averill et al. |

| | | | | | | |
|---|---|---|---|---|---|---|
| 5,573,401 | A | 11/1996 | Davidson et al. | 6,253,443 B1 | 7/2001 | Johnson |
| 5,593,451 | A | 1/1997 | Averill et al. | 6,273,891 B1 | 8/2001 | Masini |
| 5,609,641 | A | 3/1997 | Johnson et al. | 6,290,726 B1 | 9/2001 | Pope et al. |
| 5,609,645 | A | 3/1997 | Vinciguerra | 6,293,971 B1 | 9/2001 | Nelson et al. |
| 5,609,646 | A | 3/1997 | Field et al. | 6,296,667 B1 | 10/2001 | Johnson et al. |
| 5,639,280 | A | 6/1997 | Warner et al. | 6,302,913 B1 | 10/2001 | Ripamonti et al. |
| 5,658,338 | A | 8/1997 | Tullos et al. | 6,306,173 B1 | 10/2001 | Masini |
| 5,658,347 | A | 8/1997 | Sarkisian et al. | 6,309,546 B1 | 10/2001 | Herrmann et al. |
| 5,658,348 | A | 8/1997 | Rohr, Jr. | 6,322,728 B1 | 11/2001 | Brodkin et al. |
| 5,665,119 | A | 9/1997 | Koller | 6,340,370 B1 | 1/2002 | Willert et al. |
| 5,676,700 | A | 10/1997 | Black et al. | 6,352,559 B1 | 3/2002 | Church |
| 5,676,704 | A | 10/1997 | Ries et al. | 6,365,092 B1 | 4/2002 | Backa et al. |
| 5,688,453 | A | 11/1997 | England et al. | 6,376,573 B1 | 4/2002 | White et al. |
| 5,702,473 | A | 12/1997 | Albrektsson et al. | 6,383,224 B1 | 5/2002 | Gie et al. |
| 5,702,477 | A | 12/1997 | Capello et al. | 6,391,251 B1 | 5/2002 | Keicher et al. |
| 5,702,483 | A | 12/1997 | Kwong | 6,416,553 B1 | 7/2002 | White et al. |
| 5,702,487 | A | 12/1997 | Averill et al. | 6,432,142 B1 | 8/2002 | Kamiya et al. |
| 5,723,011 | A | 3/1998 | Devanathan et al. | 6,443,991 B1 | 9/2002 | Running |
| 5,723,014 | A | 3/1998 | Laurent et al. | 6,447,543 B1 | 9/2002 | Studer et al. |
| 5,725,587 | A | 3/1998 | Garber | 6,447,550 B1 | 9/2002 | Hunter et al. |
| 5,728,510 | A | 3/1998 | White | 6,454,811 B1 | 9/2002 | Sherwood et al. |
| 5,734,959 | A | 3/1998 | Krebs et al. | 6,458,161 B1 | 10/2002 | Gibbs et al. |
| 5,755,743 | A | 5/1998 | Volz et al. | 6,461,385 B1 | 10/2002 | Gayer et al. |
| 5,755,806 | A | 5/1998 | Stalcup et al. | 6,475,243 B1 | 11/2002 | Sheldon et al. |
| 5,782,928 | A | 7/1998 | Ries et al. | 6,497,727 B1 | 12/2002 | Pope et al. |
| 5,782,929 | A | 7/1998 | Sederholm | 6,506,192 B1 | 1/2003 | Gertzman et al. |
| 5,798,308 | A | 8/1998 | Chatterjee et al. | 6,508,841 B2 | 1/2003 | Martin et al. |
| 5,824,107 | A | 10/1998 | Tschirren | 6,520,995 B2 | 2/2003 | Church |
| 5,824,108 | A | 10/1998 | Huebner | 6,527,774 B2 | 3/2003 | Lieberman |
| 5,863,295 | A | 1/1999 | Averill et al. | 6,527,807 B1 | 3/2003 | O'Neil et al. |
| 5,871,548 | A | 2/1999 | Sanders et al. | 6,527,809 B1 | 3/2003 | Doursounian et al. |
| 5,879,398 | A | 3/1999 | Swarts et al. | 6,530,958 B1 | 3/2003 | Cima et al. |
| 5,879,399 | A | 3/1999 | Church | 6,537,321 B1 | 3/2003 | Horber |
| 5,879,401 | A | 3/1999 | Besemer et al. | 6,558,428 B2 | 5/2003 | Park |
| 5,879,404 | A | 3/1999 | Bateman et al. | 6,572,655 B1 | 6/2003 | Johnson |
| 5,879,405 | A | 3/1999 | Ries et al. | 6,585,772 B2 | 7/2003 | Hunter et al. |
| 5,888,205 | A | 3/1999 | Pratt et al. | 6,592,622 B1 | 7/2003 | Ferguson |
| 5,904,720 | A | 5/1999 | Farrar et al. | 6,605,293 B1 | 8/2003 | Giordano et al. |
| 5,916,268 | A | 6/1999 | Schollner et al. | 6,605,648 B1 | 8/2003 | Johnson et al. |
| 5,925,077 | A | 7/1999 | Williamson et al. | 6,610,097 B2 | 8/2003 | Serbousek et al. |
| 5,926,685 | A | 7/1999 | Krebs et al. | 6,613,093 B2 | 9/2003 | DeCarlo, Jr. et al. |
| 5,931,870 | A | 8/1999 | Cuckler et al. | 6,620,200 B1 | 9/2003 | Descamps et al. |
| 5,938,702 | A | 8/1999 | Lopez et al. | 6,621,039 B2 | 9/2003 | Wang et al. |
| 5,972,032 | A | 10/1999 | Lopez et al. | 6,626,947 B2 | 9/2003 | Lester et al. |
| 5,976,148 | A | 11/1999 | Charpenet et al. | 6,626,950 B2 | 9/2003 | Brown et al. |
| 5,981,828 | A | 11/1999 | Nelson et al. | 6,641,616 B1 | 11/2003 | Grundei |
| 5,989,293 | A | 11/1999 | Cook et al. | 6,645,206 B1 | 11/2003 | Zdeblick et al. |
| 6,008,432 | A | 12/1999 | Taylor | 6,652,586 B2 | 11/2003 | Hunter et al. |
| 6,013,104 | A | 1/2000 | Kampner | 6,660,040 B2 | 12/2003 | Chan et al. |
| 6,022,509 | A | 2/2000 | Matthews et al. | 6,660,224 B2 | 12/2003 | Lefebvre et al. |
| 6,042,611 | A | 3/2000 | Noiles | RE38,409 E | 1/2004 | Noiles |
| 6,042,612 | A | 3/2000 | Voydeville | 6,676,704 B1 | 1/2004 | Pope et al. |
| 6,049,054 | A | 4/2000 | Panchison et al. | 6,676,892 B2 | 1/2004 | Das et al. |
| 6,063,442 | A | 5/2000 | Cohen et al. | 6,682,566 B2 | 1/2004 | Draenert et al. |
| 6,066,176 | A | 5/2000 | Oshida | 6,682,567 B1 | 1/2004 | Schroeder |
| 6,087,553 | A | 7/2000 | Cohen et al. | 6,686,437 B2 | 2/2004 | Buchman et al. |
| 6,099,529 | A | 8/2000 | Gertzman et al. | 6,695,884 B1 | 2/2004 | Townley |
| 6,129,765 | A | 10/2000 | Lopez et al. | 6,696,073 B2 | 2/2004 | Boyce et al. |
| 6,132,469 | A | 10/2000 | Schroeder | 6,709,462 B2 | 3/2004 | Hanssen |
| 6,132,674 | A | 10/2000 | Compton et al. | 6,725,901 B1 | 4/2004 | Kramer et al. |
| 6,136,029 | A | 10/2000 | Johnson et al. | 6,726,723 B2 | 4/2004 | Running |
| 6,139,574 | A | 10/2000 | Vacanti et al. | 6,726,725 B2 | 4/2004 | Hunter et al. |
| 6,143,036 | A | 11/2000 | Comfort | 6,758,864 B2 | 7/2004 | Storer et al. |
| 6,143,293 | A | 11/2000 | Weiss et al. | 6,770,099 B2 | 8/2004 | Andriacchi et al. |
| 6,149,689 | A | 11/2000 | Grundei | 6,783,551 B1 | 8/2004 | Metzger et al. |
| 6,152,962 | A | 11/2000 | DeCarlo, Jr. | 6,800,094 B2 | 10/2004 | Burkinshaw |
| 6,162,257 | A | 12/2000 | Gustilo et al. | 6,811,569 B1 | 11/2004 | Afriat et al. |
| 6,165,222 | A | 12/2000 | Hoeppner et al. | 6,827,742 B2 | 12/2004 | Hayes, Jr. et al. |
| 6,176,879 | B1 | 1/2001 | Reischl et al. | 6,840,960 B2 | 1/2005 | Bubb |
| 6,187,050 | B1 | 2/2001 | Khalili et al. | 6,866,685 B2 | 3/2005 | Chan et al. |
| 6,192,272 | B1 | 2/2001 | Fiedler | 6,869,447 B2 | 3/2005 | Lee et al. |
| 6,193,761 | B1 | 2/2001 | Treacy | 6,896,703 B2 | 5/2005 | Barbieri et al. |
| 6,197,065 | B1 | 3/2001 | Martin et al. | 6,908,486 B2 | 6/2005 | Lewallen |
| 6,203,844 | B1 | 3/2001 | Park | 6,916,342 B2 | 7/2005 | Frederick et al. |
| 6,206,924 | B1 | 3/2001 | Timm | 6,923,833 B2 | 8/2005 | Wasielewski |
| 6,217,620 | B1 | 4/2001 | Park | 6,926,740 B2 | 8/2005 | Lewis et al. |
| 6,228,121 | B1 | 5/2001 | Khalili | 6,945,448 B2 | 9/2005 | Medlin et al. |
| 6,231,612 | B1 | 5/2001 | Balay et al. | 6,981,991 B2 | 1/2006 | Ferree |
| 6,240,616 | B1 | 6/2001 | Yan | 7,141,073 B2 | 11/2006 | May et al. |

| | | |
|---|---|---|
| 7,147,819 B2 | 12/2006 | Bram et al. |
| 7,156,880 B2 | 1/2007 | Evans et al. |
| 7,166,133 B2 | 1/2007 | Evans et al. |
| 7,189,263 B2 | 3/2007 | Erbe et al. |
| 7,192,448 B2 | 3/2007 | Ferree |
| 7,351,371 B2 | 4/2008 | Nelles et al. |
| 2001/0011190 A1 | 8/2001 | Park |
| 2001/0013166 A1 | 8/2001 | Yan |
| 2001/0030035 A1 | 10/2001 | Oda |
| 2002/0016635 A1 | 2/2002 | Despres, III et al. |
| 2002/0040245 A1 | 4/2002 | Lester et al. |
| 2002/0062154 A1 | 5/2002 | Ayers |
| 2002/0068980 A1 | 6/2002 | Serbousek et al. |
| 2002/0071827 A1 | 6/2002 | Petersen et al. |
| 2002/0123750 A1 | 9/2002 | Eisermann et al. |
| 2002/0139504 A1 | 10/2002 | Klein |
| 2002/0143403 A1 | 10/2002 | Vaidyanathan et al. |
| 2002/0151983 A1 | 10/2002 | Shetty |
| 2002/0197178 A1 | 12/2002 | Yan |
| 2003/0001282 A1 | 1/2003 | Meynen et al. |
| 2003/0013989 A1 | 1/2003 | Obermiller et al. |
| 2003/0033020 A1 | 2/2003 | Hunter et al. |
| 2003/0049299 A1 | 3/2003 | Malaviya et al. |
| 2003/0050703 A1 | 3/2003 | Harris et al. |
| 2003/0050705 A1 | 3/2003 | Cueille et al. |
| 2003/0069639 A1 | 4/2003 | Sander et al. |
| 2003/0083741 A1 | 5/2003 | Woo et al. |
| 2003/0105529 A1 | 6/2003 | Synder et al. |
| 2003/0111752 A1 | 6/2003 | Wood et al. |
| 2003/0114936 A1 | 6/2003 | Sherwood et al. |
| 2003/0135281 A1 | 7/2003 | Hanssen |
| 2003/0144741 A1 | 7/2003 | King et al. |
| 2003/0144742 A1 | 7/2003 | King et al. |
| 2003/0153981 A1 | 8/2003 | Wang et al. |
| 2003/0153982 A1 | 8/2003 | Pria |
| 2003/0155686 A1 | 8/2003 | Hawkins et al. |
| 2003/0163202 A1 | 8/2003 | Lakin |
| 2003/0163203 A1 | 8/2003 | Nycz et al. |
| 2003/0171818 A1 | 9/2003 | Lewallen |
| 2003/0200837 A1 | 10/2003 | Matsuura et al. |
| 2003/0220696 A1 | 11/2003 | Levine et al. |
| 2003/0232124 A1 | 12/2003 | Medlin et al. |
| 2003/0236573 A1 | 12/2003 | Evans et al. |
| 2004/0054418 A1 | 3/2004 | McLean et al. |
| 2004/0054421 A1 | 3/2004 | McLean |
| 2004/0064192 A1 | 4/2004 | Bubb |
| 2004/0072010 A1 | 4/2004 | Date et al. |
| 2004/0083004 A1 | 4/2004 | Wasielewski |
| 2004/0088038 A1 | 5/2004 | Dehnad et al. |
| 2004/0098127 A1 | 5/2004 | Charlebois et al. |
| 2004/0102854 A1 | 5/2004 | Zhu |
| 2004/0109853 A1 | 6/2004 | McDaniel |
| 2004/0122521 A1 | 6/2004 | Lee et al. |
| 2004/0126265 A1 | 7/2004 | Takiguchi |
| 2004/0126583 A1 | 7/2004 | Nakamura et al. |
| 2004/0137218 A1 | 7/2004 | Liu et al. |
| 2004/0166340 A1 | 8/2004 | Cairns et al. |
| 2004/0172137 A1 | 9/2004 | Blaylock et al. |
| 2004/0186553 A1 | 9/2004 | Yan |
| 2004/0199258 A1 | 10/2004 | Macara |
| 2004/0199260 A1 | 10/2004 | Pope et al. |
| 2004/0210316 A1 | 10/2004 | King et al. |
| 2004/0225369 A1 | 11/2004 | Lakin et al. |
| 2004/0225371 A1 | 11/2004 | Roger |
| 2004/0229029 A1 | 11/2004 | Bowles et al. |
| 2004/0238410 A1 | 12/2004 | Inoue et al. |
| 2004/0243133 A1 | 12/2004 | Materna |
| 2005/0004677 A1 | 1/2005 | Johnson |
| 2005/0004678 A1 | 1/2005 | Richards |
| 2005/0004680 A1 | 1/2005 | Saladino et al. |
| 2005/0010303 A1 | 1/2005 | Nogier |
| 2005/0025656 A1 | 2/2005 | Bhaduri et al. |
| 2005/0031704 A1 | 2/2005 | Ahn |
| 2005/0032025 A1 | 2/2005 | Bhaduri et al. |
| 2005/0035052 A1 | 2/2005 | Kelly et al. |
| 2005/0048193 A1 | 3/2005 | Li et al. |
| 2005/0049713 A1 | 3/2005 | Garber et al. |
| 2005/0060040 A1 | 3/2005 | Auxepaules et al. |
| 2005/0065307 A1 | 3/2005 | King et al. |
| 2005/0065604 A1 | 3/2005 | Stoll |
| 2005/0071015 A1 | 3/2005 | Sekel |
| 2005/0085820 A1 | 4/2005 | Collins et al. |
| 2005/0085915 A1 | 4/2005 | Steinberg |
| 2005/0087915 A1 | 4/2005 | Pope et al. |
| 2005/0090905 A1 | 4/2005 | Hawkins et al. |
| 2005/0100470 A1 | 5/2005 | Lefebvre et al. |
| 2005/0107883 A1 | 5/2005 | Goodfried et al. |
| 2005/0145364 A1 | 7/2005 | Nakajima |
| 2005/0149199 A1 | 7/2005 | Steinberg |
| 2005/0171614 A1 | 8/2005 | Bacon |
| 2005/0184134 A1 | 8/2005 | Charlebois et al. |
| 2005/0234559 A1 | 10/2005 | Fernandez et al. |
| 2005/0246032 A1 | 11/2005 | Bokros et al. |
| 2006/0002810 A1 | 1/2006 | Grohowski |
| 2006/0003179 A1 | 1/2006 | Wang et al. |
| 2006/0018942 A1 | 1/2006 | Rowe et al. |
| 2006/0241776 A1 | 10/2006 | Brown et al. |
| 2006/0241781 A1 | 10/2006 | Brown et al. |
| 2007/0021838 A1 | 1/2007 | Dugas et al. |
| 2007/0129809 A1 | 6/2007 | Meridew et al. |
| 2007/0173948 A1 | 7/2007 | Meridew et al. |
| 2007/0196230 A1 | 8/2007 | Hamman et al. |
| 2007/0250175 A1 | 10/2007 | Meridew et al. |
| 2007/0264152 A1 | 11/2007 | Zhao |
| 2008/0147187 A1 | 6/2008 | Bollinger et al. |
| 2009/0084491 A1 | 4/2009 | Uthgenannt et al. |

FOREIGN PATENT DOCUMENTS

| | | |
|---|---|---|
| DE | 2404214 | 8/1974 |
| DE | 3130732 | 5/1983 |
| DE | 3205526 | 9/1983 |
| DE | 8612735 | 3/1989 |
| DE | 41 33 433 | 5/1993 |
| DE | 19726961 | 11/1998 |
| EP | 0 214 885 | 7/1986 |
| EP | 0214885 | 3/1987 |
| EP | 0 378 928 | 7/1990 |
| EP | 0378928 | 7/1990 |
| EP | 0 538 987 | 4/1993 |
| EP | 0538987 | 4/1993 |
| EP | 0551794 | 7/1993 |
| EP | 0577179 | 1/1994 |
| EP | 0612509 | 8/1994 |
| EP | 0648478 | 4/1995 |
| EP | 0 807 426 | 11/1997 |
| EP | 0806921 | 11/1997 |
| EP | 0 985 386 | 3/2000 |
| EP | 0985386 | 3/2000 |
| EP | 1082949 | 3/2001 |
| EP | 1 236 450 | 9/2002 |
| EP | 0 806 921 | 1/2003 |
| EP | 1312323 | 5/2003 |
| EP | 1 384 456 | 1/2004 |
| EP | 1421918 | 5/2004 |
| EP | 1 430 856 | 6/2004 |
| EP | 1430856 | 6/2004 |
| FR | 2 148 322 | 3/1973 |
| FR | 2775586 | 9/1999 |
| FR | 2803740 | 7/2001 |
| GB | 2001247 | 1/1979 |
| WO | WO 92/18069 | 4/1992 |
| WO | WO-92/18069 | 10/1992 |
| WO | WO 96/23459 | 1/1996 |
| WO | WO-96/13233 | 5/1996 |
| WO | WO 96/13233 | 5/1996 |
| WO | WO-96/23459 | 8/1996 |
| WO | WO-00/38598 | 7/2000 |
| WO | WO 00/38598 | 7/2000 |
| WO | WO-01/70141 | 9/2001 |
| WO | WO-02/07652 | 1/2002 |
| WO | WO 02/07652 | 1/2002 |
| WO | WO-2004069107 | 8/2004 |
| WO | WO 2004/080340 | 9/2004 |
| WO | WO-2004/080340 | 9/2004 |
| WO | WO-2006007861 | 1/2006 |

OTHER PUBLICATIONS

Bram, Martin, et al., High-Porosity Titanium, Stainless Steel, and

Superalloy Parts, Advanced Engineering Materials 2000, 2, No. 4, 196-199.

Oliveira, M. V., et al., Porous Structure Characterization in Titanium Coating for Surgical Implants, © 2002, Materials Research, vol. 5, No. 3, 269-273.

Wen, C. E., et al., Novel titanium foam for bone tissue engineering, J. Mater. Res., vol. 17, No. 10, Oct. 2002, 2633-2639.

Wen, C. E., et al., Processing and mechanical properties of autogenous titanium implant materials, Journal of Materials Science: Materials in Medicine 13 (2002), 397-401.

Wen, C. E., Processing of biocompatible porous Ti and Mg, Scripta Materialia 45 (2001) 1147-1153.

Wheeler, K. R., et al., Porous Metals as a Hard Tissue Substitute. Part II. Porous Metal Properties, Biomat., Med. Dev., Art. Org., 1(2), 337-348 (1973).

"Magnum™ large metal articulation, Surgical Technique" brochure, Biomet Orthopedics, Inc., 2004 (12 pages).

Bram, Martin et al., High-Porosity Titanium, Stainless Steel, and Superalloy Parts, Advanced Engineering Materials 2000, 2, No. 4, 196-199.

Oliveira, M.V., et al., Porous Structure Characterization in Titanium Coating for Surgical Implants, ® 2002. Materials Research, vol. 5, No. 3, 269-273.

Wen, C.E., et al., Novel titanium foam for bone tissue engineering, J. Mater. Res., vol. 17, No. 10. Oct. 2002, 2633-2639.

Wen, C.E., et al., Processing and mechanical properties of autogenous titanium implant materials, Journal of Materials Science: Materials in Medicine 13 (2002), 397-401.

Wen, C.E., Processing of biocompatible porous Ti and Mg, Scripta Materialia 45 (2001) 1147-1153.

Wheeler, K.R., et al., Porous Metals as a Hard Tissue Substitute. Part II. Porous Metal Properties, Biomat., Med. Dev., Art. Org., 1(2). 337-348 (1973).

Michael S. Bradford, M.D. and Wayne G. Paprosky, M.D., F.A.C.S., Total Acetabular Transplant Allograft Reconstruction of the Severely Deficient Acetabulum, Sunrise Hospital and Medical Center, Las Vegas, NV and Rush-Presbyterian-St. Lukes Medical Center, Chicago, IL, 1995 by W.B. Saunders Company, pp. 1-15.

European Search Report mailed Jul. 12, 2007 for European Application No. 07250588.6.

International Search Report and Written Opinion for PCT/US2007/03811 mailed Sep. 27, 2007.

International Search Report and Written Opinion for PCT/US2008/002372 mailed Jul. 30, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

Laptev, A. et al. "Study of Production Route for Titanium Parts Combining Very High Porosity and Complex Shape" Powder Metallurgy, vol. 47, No. 1 (2004), pp. 85-92.

* cited by examiner

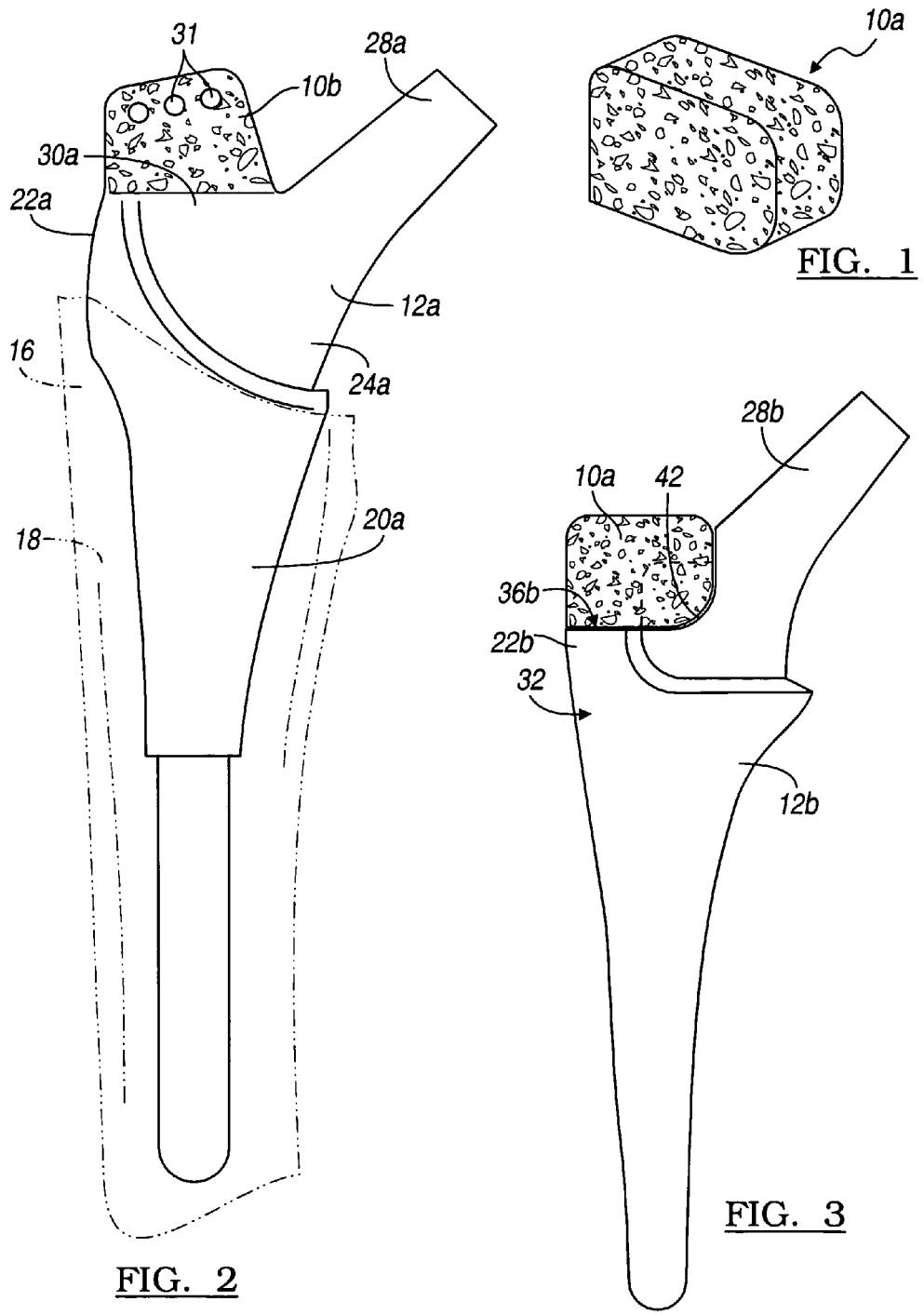

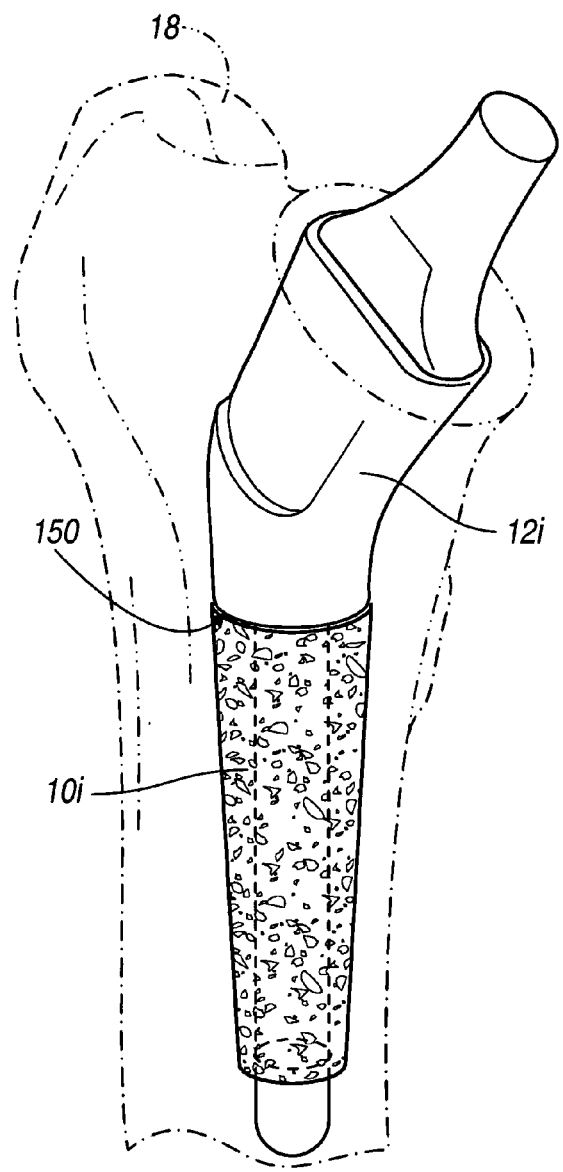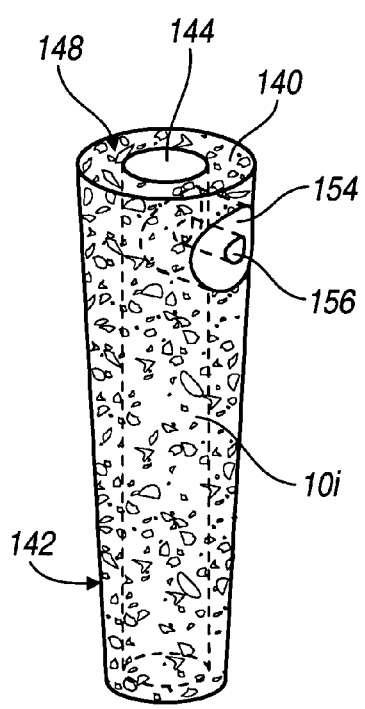
FIG. 13
FIG. 14

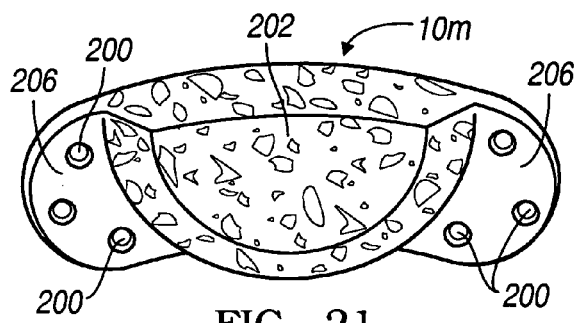
FIG. 21
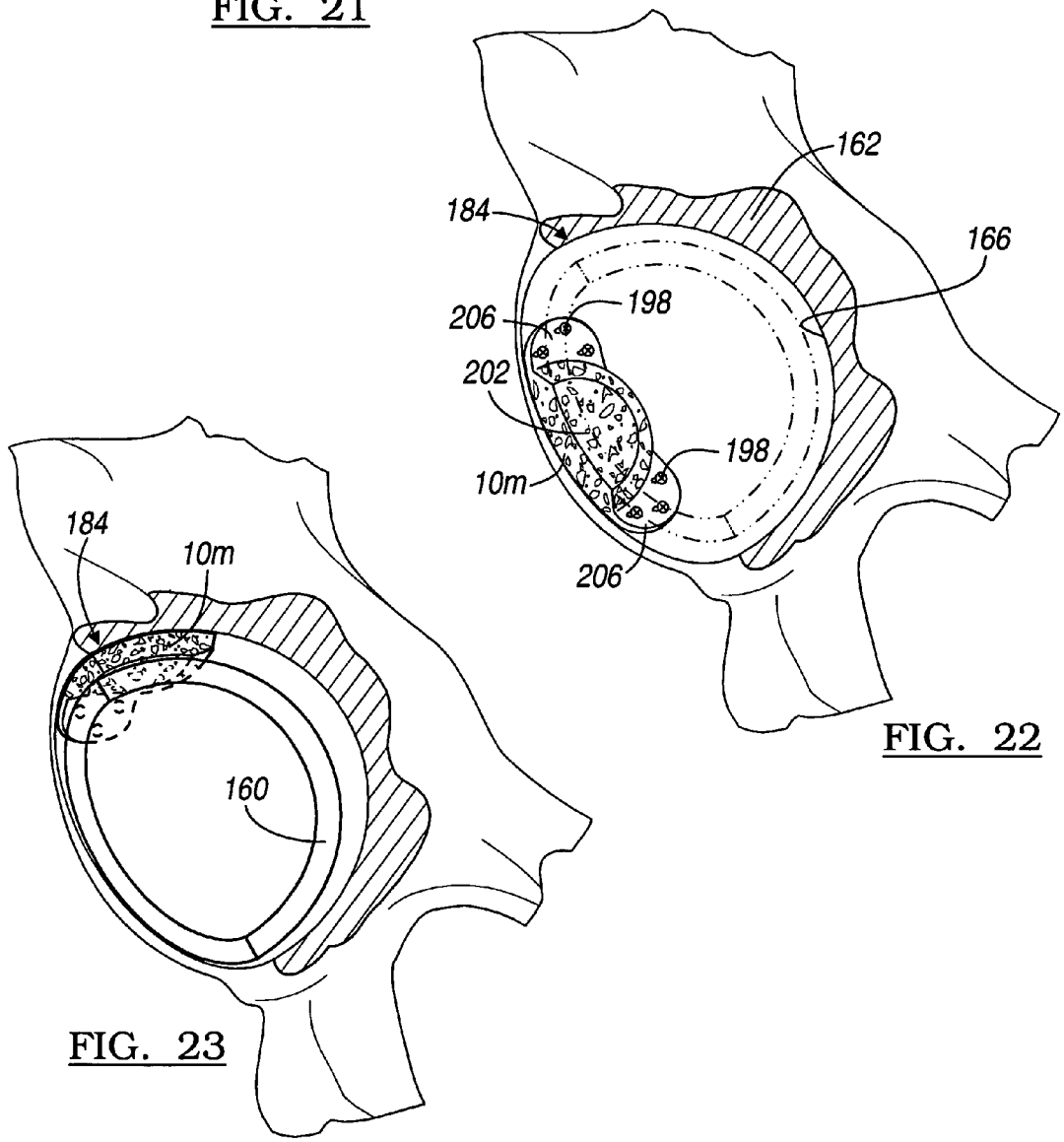
FIG. 22
FIG. 23

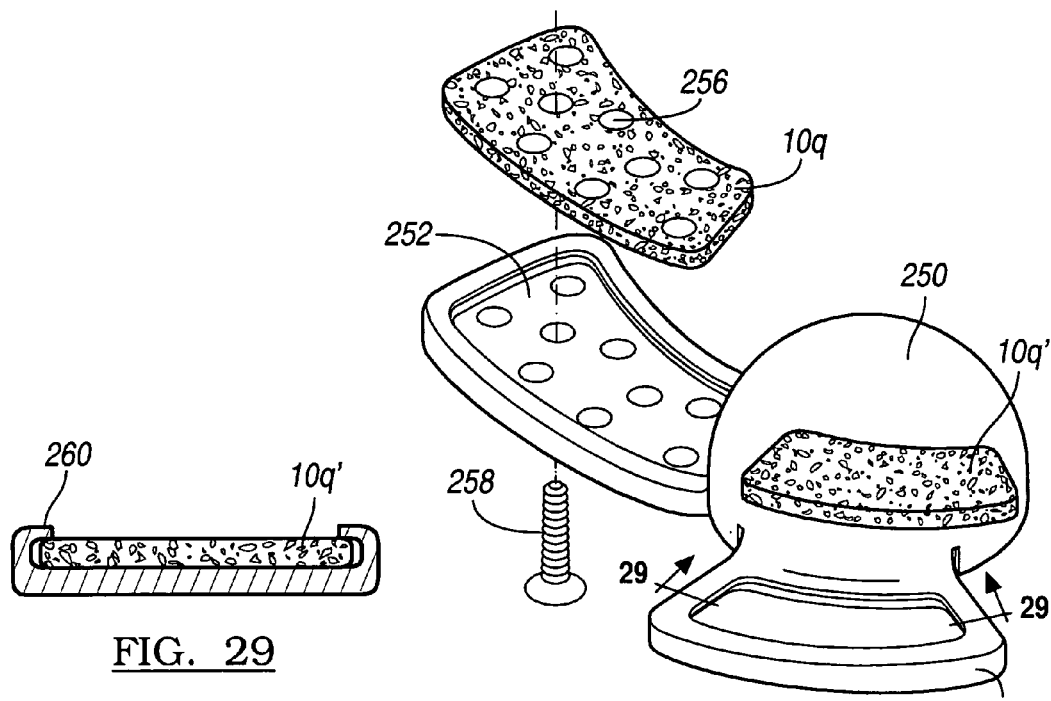
FIG. 29
FIG. 28
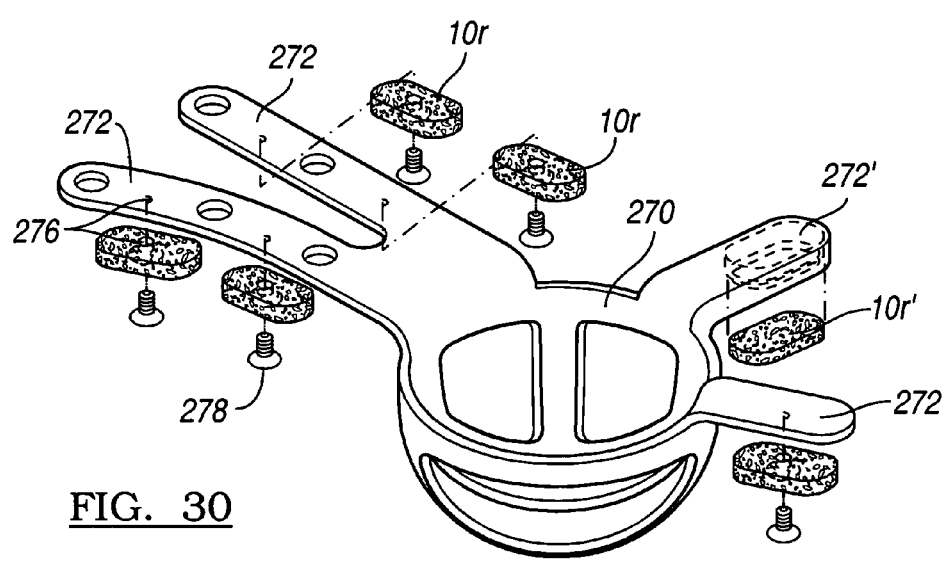
FIG. 30

1

APPARATUS FOR USE OF POROUS IMPLANTS

CROSS-REFERENCE TO RELATED APPLICATIONS

This application is a continuation-in-part of U.S. patent application Ser. No. 11/357,868, filed Feb. 17, 2006. The disclosures of the above application is incorporated herein by reference.

FIELD OF THE INVENTION

The present invention relates to porous implants and more particularly to a method of implanting porous implants as augments for replacing removed portions of bone.

INTRODUCTION

Porous coated implants have been used to promote biologic fixation of surrounding bony tissue. In one example, porous material may be coated on an exterior surface of a prosthetic implant to encourage ingrowth of surrounding bone into the pore spaces of the porous material. Typically, the porous coating may comprise stainless steel, titanium, titanium alloys, tantalum, cobalt-chromium alloys, ceramics, polymers and other materials that are suited for use in a biocompatible environment. Various joining methods have been employed to attach the porous coating to a desired prosthetic implant. For example, soldering, brazing, adhesive joining, laser welding, diffusion bonding, metallurgic bonds and mechanical joining have been shown to suitably attach the porous material to a desired implant.

In other examples, implants may be used as augments to fill in a gap between a host bone and an implant. In this way, it may be desirable to incorporate a porous surface to encourage bone and/or soft tissue ingrowth. In one particular example, it may be desirable to build up an acetabular socket that has been sunken in. In one approach, an acetabular cup may be implanted that defines a thicker cross-section at an apex as compared to a rim portion to accommodate for a sunken in acetabular socket.

SUMMARY OF THE INVENTION

An acetabular cup assembly implantable at an acetabular socket can include an acetabular cup defining a partially spherical bone engaging surface and having a uniform thickness. A spacer can include a body portion formed of porous metal and define a radial support surface. The porous metal can be adapted to receive bone ingrowth through interstitial space at pores defined therein. The spacer can further comprise a piercing portion adapted to be advanced into the acetabular socket. The spacer can bridge a gap defined between the acetabular socket and the acetabular cup. Filler can be disposed between the acetabular cup and the acetabular socket in areas adjacent to the spacer such that the spacer and the filler collectively define a continuous support surface adapted to support the acetabular cup at the bone engaging surface.

According to additional features, an acetabular cup assembly can include an augment including a solid flange portion. The solid flange portion can be adapted to rest around a rim region of the acetabular socket in an implanted position. The porous metal portion can be adapted to rest intermediate the acetabular cup and the acetabular socket to bridge a gap defined between the acetabular socket and the acetabular cup. A fastener can selectively couple the augment to the acetabular socket.

According to additional features, an acetabular cup assembly can include a flange integrally formed with the acetabular cup for fastening to surrounding pelvis of the acetabulum. The flange can define a receptacle on a pelvis engaging surface. An augment formed of porous metal and adapted to receive bone ingrowth through interstitial space at pores defined therein can be adapted to be received at the receptacle in an installed position. The augment can be located intermediate the flange and the surrounding pelvis of the acetabulum in an implanted position.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of an exemplary porous augment according to the present teachings;

FIG. 2 is a lateral view of an exemplary porous insert shown connected to an exemplary hip stem according to the present teachings;

FIG. 3 is a lateral view of an exemplary porous insert shown connected to another exemplary hip stem according to the present teachings;

FIG. 13 is a perspective view of another porous augment shown cooperating with an exemplary hip stem according to the present teachings;

FIG. 14 is a perspective view of the porous augment illustrated in FIG. 13 shown removed from the hip stem;

FIG. 21 is a perspective view of another augment according to the present teachings;

FIG. 22 is a perspective view of an exemplary acetabulum built up with the augments of FIG. 21 according to a second example;

FIG. 23 is a perspective view of an exemplary acetabular cup implanted at an acetabulum built up with augments of FIG. 21 according to one example;

FIG. 28 is a perspective view of an exemplary acetabular cup and attachable augments according to the present teachings;

FIG. 29 is a cross-sectional view of the acetabular cup and augment of FIG. 28 taken along line 29-29; and FIG. 30 is an exploded perspective view of another exemplary cup and attachable augments according to the present teachings.

DETAILED DESCRIPTION OF THE PREFERRED EMBODIMENTS

Figure 5:
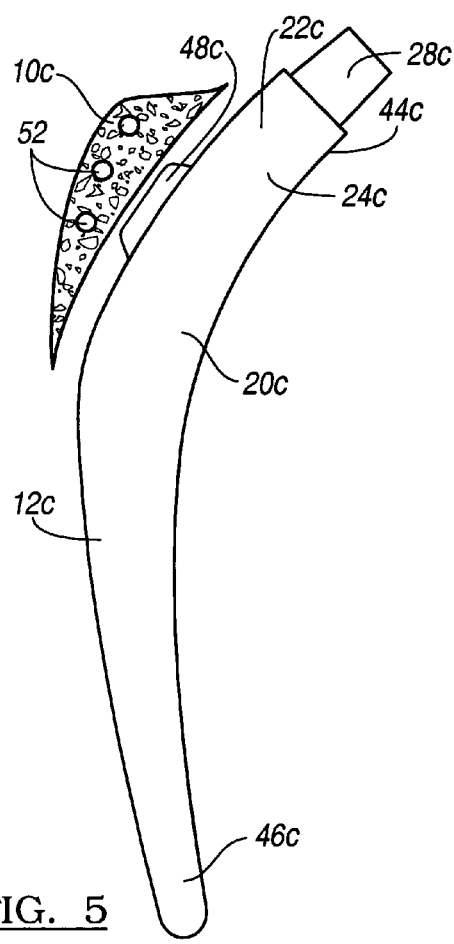
FIG. 5 is a lateral view of the porous augment of FIG. 4 shown connected to an exemplary hip stem according to the present teachings.

The following description of the embodiment(s) is merely exemplary in nature and is in no way intended to limit the invention, its application, or uses. Moreover, while various shaped metal augments or inserts and certain types of inserts are illustrated, they are merely exemplary in that any shape or any type of implant may include the metal augments.

As used herein, the terms insert, augment and spacer have been used interchangeably. While one term may be more applicable to a given application, it is appreciated that various characteristics associated with an insert, augment and/or spacer may be similarly applicable. With initial reference to FIGS. 1-30, a series of exemplary porous metal inserts, augments or spacers according to the present teachings are shown and identified generally at 10a-10r, respectively. As will be described in greater detail, the porous metal augments 10a-10r, shown in FIGS. 1-30, may be employed in cooperation with an implantable prosthesis and provide a suitable surface area for encouraging ingrowth of natural bone and/or soft tissue. In addition, the porous metal augments 10a-10r may be adapted to provide mechanical strength in a load bearing application, or simply be employed as a spacer or filler to build up an area around an implant such as around an acetabular socket. In this way, the porous metal augments disclosed herein may also be load bearing in applications having compression, tension, cantilever, static or dynamic loads. In general, the porous metal is adapted to receive bone ingrowth through interstitial space at pores defined in the porous metal.

According to the present teachings, the porous metal used in the augments 10a-10r may comprise stainless steel, titanium, titanium alloys, cobalt-chromium alloys and other materials that are suited for use in a biocompatible environment such as disposed on an implantable bone prosthesis. Various compositions and methods of making such porous metal may be found in co-pending applications, now published as U.S. Publication No. 2006/0241776, published Oct. 26, 2006; U.S. Pat. No. 7,597,715, issued Oct. 6, 2009 and U.S. Pat. No. 7,635,447, issued Dec. 22, 2009, all of which are also assigned to Biomet Manufacturing Corp., of Warsaw Ind., which are incorporated herein by reference.

Turning now to FIGS. 1-3, a method of utilizing an augment 10a and 10b with an implantable bone prosthesis will be described. The exemplary bone prosthesis shown is a femoral hip stem 12a and 12b, respectively. It is appreciated that while the exemplary bone prosthesis is shown as a femoral hip stem 12a and 12b, other prosthesis may similarly be employed. As illustrated in FIG. 2 natural bone 16 of a femur 18 is shown prepared for the reception of the prosthesis 12a. It is appreciated that the prosthesis 12b (FIG. 3) may be similarly adapted for implantation into the femur 18 of FIG. 2. The hip stem 12a generally includes a stem portion 20a, a proximal lateral 22a, a calcar 24a, and a neck region 28a. In one example shown in FIG. 2, the augment 10b may be integrally formed with the hip stem 12a. In the example shown, the augment 10b may be formed at a superior surface 30a of the proximal lateral 22a and define openings 31. In one example, the openings 31 may be used to attach flexible members such as suture thereat. With reference to FIG. 3, the hip prosthesis 12b is shown. The hip prosthesis 12b may include a bi-planar taper 32. The bi-planar taper 32 may allow the femoral hip stem 12b to function like a wedge, which can promote bone-preserving stress to transfer from the femoral hip stem 12b to the natural bone. In one example, the augment 10a may be modular such that the augment 10a may be added interoperatively. In the example shown, a superior surface 36b of the proximal lateral 22b provides a notch or receiving area 42 for accepting the augment 10a. The augment 10a may be attached to the implant 12b by any suitable method such as bone cement and/or mechanical fasteners.

Figure 6:
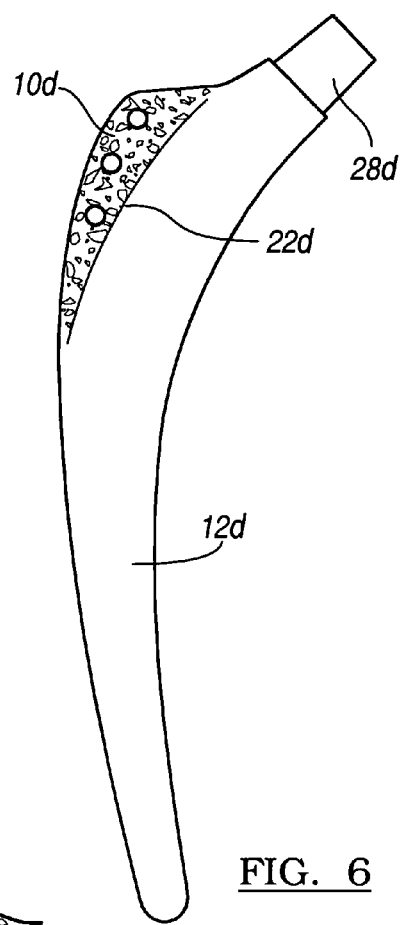
FIG. 6 is a lateral view of an exemplary hip stem having an integrally formed porous metal augment.
Figure 4:
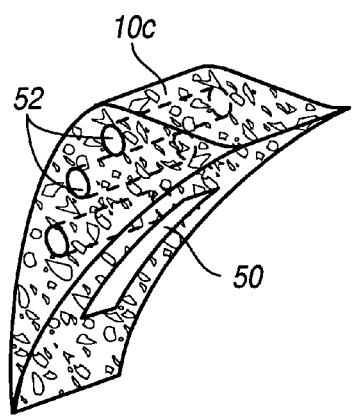
FIG. 4 is a perspective view of another exemplary porous augment according to the present teachings.

Turning now to FIGS. 4-6, another porous metal augment and method of utilizing the porous metal augment will be described. The porous metal augments 10c and 10d may be adapted for use with a tapered femoral hip stem 12c. One such tapered femoral hip stem 12c is the PLR™ (Proximal Loading Revision) revision stem offered by Biomet Inc., of Warsaw, Ind. In general, the hip stem 12c may be gradually tapered between a proximal end 44c and a distal end 46c. The hip stem 12c generally includes a stem portion 20c, a proximal lateral 22c, a calcar 24c, and a neck region 28c. In one example the shaft angle of the neck region 28c may be 135° allowing the surgeon to recreate the patient's normal anatomic offset which may reduce the chance for dislocation and subluxation. Other angles may be used. In one example, a flange 48c may be formed on the proximal lateral portion 22c of the stem 12c. A complementary recess 50 (FIG. 4) may be formed on the augment 10c such that the flange 48c of the stem 12c may nest within the recess 50 in an installed position. The augment 10c may be secured to the flange 48c such as by bone cement or mechanical fasteners. Again, the porous material enables soft tissue ingrowth.

According to additional features, the augment 10c may define passages 52. The passages 52 may allow the surgeon to create additional stability by suturing soft tissue to the stem 12c. According to another example as shown in FIG. 6, the augment 10d may be integrally formed with the stem 12d at the proximal lateral portion 22d.

Figure 7:
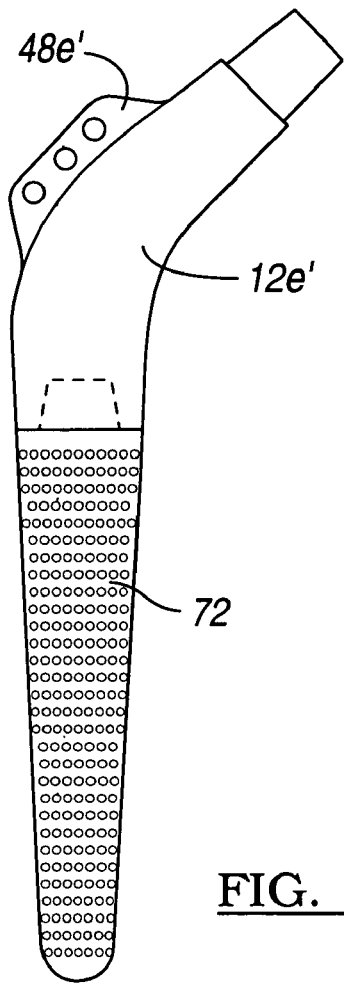
FIG. 7 is a lateral view of an exemplary hip stem according to the present teachings.
Figure 8:
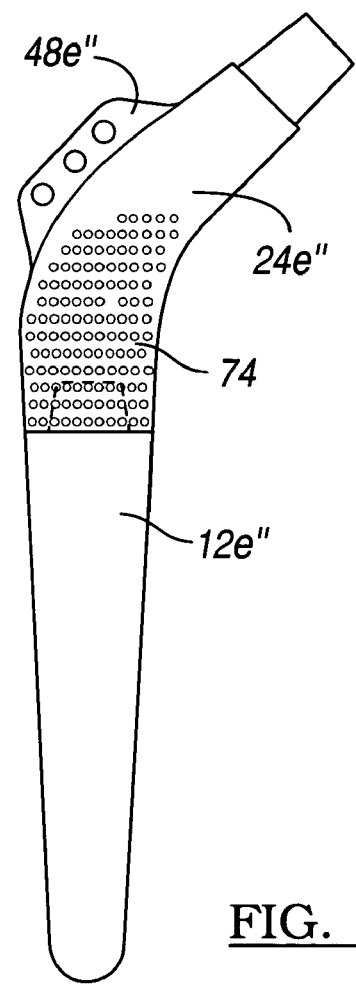
FIG. 8 is a lateral view of another exemplary hip stem according to the present teachings.
Figure 9:
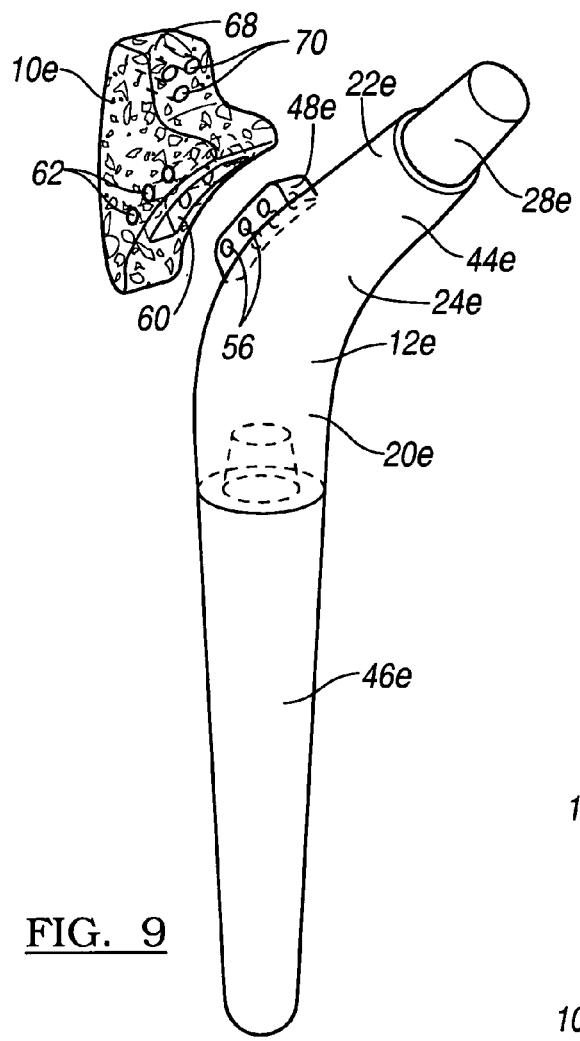
FIG. 9 is a perspective view of another porous augment shown connected to an exemplary hip stem according to the present teachings.

Turning now to FIGS. 7-10, porous metal augments 10e, 10f, 10f' and 10f" and a method of utilizing the porous metal augments 10e, 10f, 10f' and 10f" will be described. The porous metal augments 10e, 10f, 10f', and 10f" may be adapted for use with a tapered femoral hip stem 12e. In general, the hip stem 12e may be gradually tapered between a proximal end 44e and a distal end 46e. The hip stem 12e generally includes a stem portion 20e, a proximal lateral 22e, a calcar 24e, and a neck region 28e. In one example, a flange 48e may be formed on the proximal lateral portion 22e of the stem 12e. The flange 48e may define a plurality of passages 56. A complementary recess 60 may be formed on the augment 10e such that the flange 56 of the stem 12e may nest within the recess 60 in an installed position. The augment 10e may be secured to the flange 48e such as by bone cement or mechanical fasteners. In one example, the augment 10e may define a plurality of complementary passages 62 for aligning with the passages 56 on the flange 48e. Flexible attachment members such as sutures (not shown) may be used to pass through the respective passages 56 and 60 when securing soft tissue to the stem 12e. The augment 10e further includes a raised superior portion 68. The raised superior portion 68 may define additional passages 70 for accepting flexible attachment members such as sutures. As shown in FIG. 7, the distal portion of the stem 12e' may include a textured surface 72 to facilitate bone ingrowth. Similarly, as shown in FIG. 8, the calcar 24e" may include a textured surface 74 to facilitate bone ingrowth.

Figure 10:
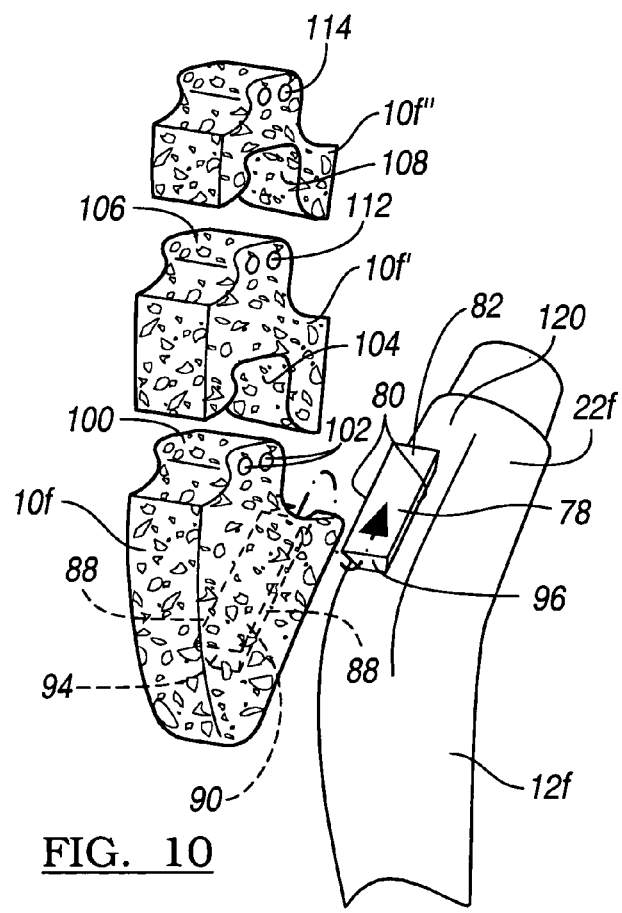
FIG. 10 is a perspective view of a series of interlocking porous augments shown connected to an exemplary hip stem according to the present teachings.

Turning now to FIG. 10, a series of interlocking augments 10f, 10f' and 10f" are shown. A retaining structure 78 is formed on the proximal lateral 22f of the hip stem 12f. It is appreciated that the retaining structure 78 may be formed at any location on the prosthesis for achieving alternate locations and/or orientations.

The retaining structure 78 generally includes a pair of tapered sidewalls 80 defining a receiving block 82 therebetween. The receiving block 82 may be adapted to slidably accept the augment 10f in a secured relationship. The augment 10f defines complementary sidewalls 88 defining a receiving channel 90 for slidably accepting the sidewalls 80 of the receiving block 82. In one implementation, the geometries of the respective sidewalls 80 and 88 allow for a clearance fit, interference fit or a press fit to ensure the augment 10f is retained by the retaining structure 78 of the prosthesis 12f. The augment 10f may further define a rear wall 94 for engaging an end 96 of the receiving block 82. In this way, no auxiliary fasteners are needed to secure the augment 10f to the prosthesis 12f, however, additional fasteners may be used as supplemental attachment if desired. The augment 10f may define a first interlocking portion 100 extending therefrom. The augment 10f may define passages 102 thereon for accepting flexible attachment members such as sutures. A second augment 10f' may define a complementary second interlocking portion 104 adapted to mate with the first interlocking portion 100 of the augment 10f and a third interlocking portion 106 adapted to mate with a fourth interlocking portion 108 of a third augment 10f". As shown, the second and third augments 10f' and 10f" may each define passages 112 and 114, respectively thereon for accepting sutures. It is appreciated that the structure of the respective interlocking portions 100, 104, 106 and 108 is merely exemplary and that other configurations may be employed for building up a desired area around the hip stem 12f.

It is appreciated that other geometries may be provided for the retaining structure 78 and associated sidewalls 80 to provide a complementary and integral retaining structure for receiving an augment. In the same way, alternate geometrical configurations may be necessary for an augment to cooperatively mate with a given retaining structure on a prosthesis. For example, while the retaining structure 78 is shown integrally formed on a greater trochanter 120 of the hip prosthesis 12f, it is appreciated that the retaining structure 78 may be configured elsewhere on the hip prosthesis 12f or on any other implantable prosthesis.

Figure 11:
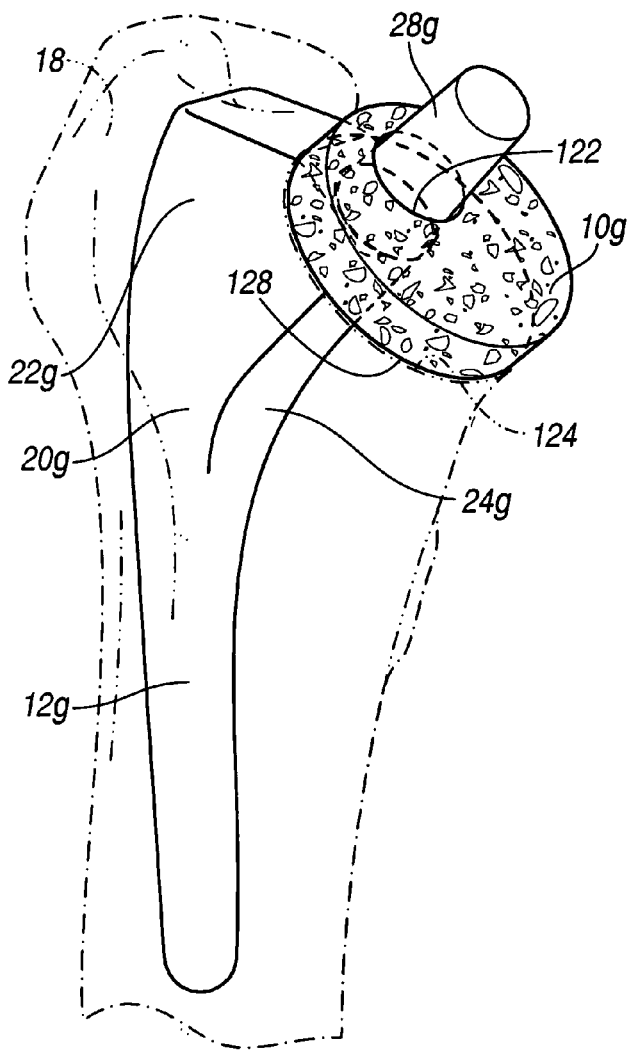
FIG. 11 is a perspective view of a porous augment shown cooperating with an exemplary hip stem according to the present teachings.

With reference now to FIG. 11, another porous metal augment and method of utilizing a porous metal augment will be described. The porous metal augment 10g may be adapted for use with a femoral hip stem 12g. The hip stem 12g generally includes a stem portion 20g, a proximal lateral 22g, a calcar portion 24g and a neck region 28g. The porous metal augment 10g may define an opening 122. The neck 28g may be passed through the opening 122 as shown in FIG. 11 in an implanted position. The porous metal augment 10g may be adapted to be at least partially supported on one portion by the calcar portion 24g of the stem 12g and at least partially supported on a second portion by a proximal femur 18. More specifically, a superior face 124 of the femur 18 may engage an inferior surface 128 of the augment 10g in an implanted position. In this way, the porous insert 10g may be adapted to facilitate tissue ingrowth and act as a vertical support to inhibit subsidence of the stem 12g into the intramedullary canal. Explained further, the augment 10g may rest atop the superior face 124 of the femur 18 and maintain the stem 12g at a supported location and therefore discourage the stem 121g from moving inferiorly in the intramedullary canal.

Figure 12:
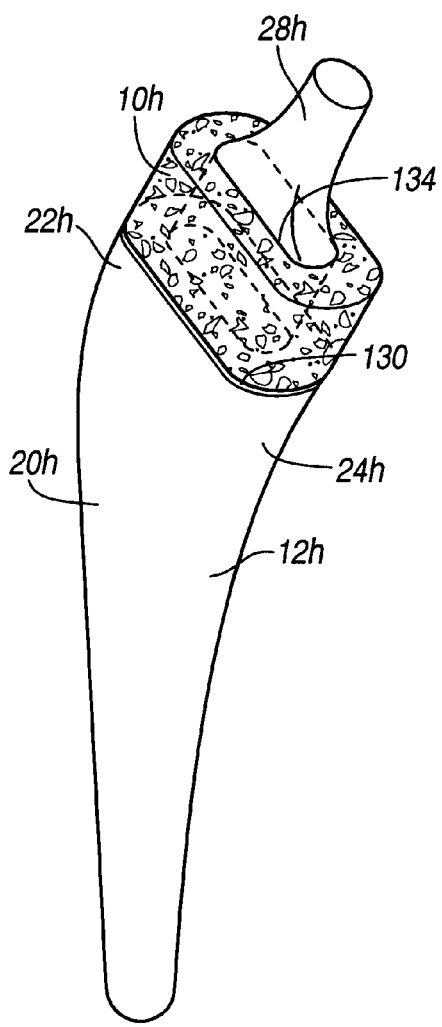
FIG. 12 is a perspective view of another porous augment shown cooperating with an exemplary hip stem according to the present teachings.

With reference to FIG. 12, another porous metal augment and method of utilizing a porous metal augment 10h will be described. The porous metal augment 10h may be adapted for use with a femoral hip stem 12h. The hip stem 12h generally includes a stem portion 20h, a proximal lateral 22h, a calcar 24h, and a neck region 28h. An annular ledge 130 may be defined at the calcar 24h. The porous metal augment 10h may be in the form of a sleeve and define a generally elongated opening 134. The neck 28h may be passed through the opening 134 as shown in FIG. 12 in an implanted position.

With reference now to FIGS. 13 and 14, an augment 10i in the form of a porous sheath or sleeve 140 is shown operatively secured to a femoral hip stem 12i. The sleeve 140 is formed of porous metal such as disclosed herein. In one example, the augment 10i may define a tapered outer surface 142 and a throughbore 144 having a constant radius along the axis of the augment 10i. In another example, the sleeve 140 may define a taper (not shown) along its axis for facilitating a press-fit around the sleeve 140 in an implanted position. The sleeve 140 may be slidably inserted around the distal stem 12i until a superior surface 148 of the sleeve 140 engages an inferior annular ledge 150 of the stem 12i. Adhesive such as bone cement may be used to secure the augment 10i to the stem 12i in a stable position. In another example, the sleeve 140 may be slidably inserted around the distal stem 12i until a press-fit or friction fit is attained thereby securing the augment 10i into a stable position. In an implanted position, the porous metal sleeve 140 provides biological fixation as bone grows up to and within the porous material. While the porous metal sleeve 140 is shown cooperatively engaged with a stem 12i of a femoral hip, it is appreciated that the sleeve 140 may be used in cooperation around other prosthesis incorporating stems such as proximal humeral replacement.

Providing a stand alone sleeve 140 allows pore size and thickness to be controlled during formation of the sleeve 140 without the concern of compromising the mechanical properties of the stem 12i as may be an issue when administering a porous coating onto the stem 12i. In one example, pore size may be increased distally down the sleeve 140 to gradually reduce the stiffness of the stem 12*i* in an assembled position (FIG. 13). In addition, the stand alone sleeve 140 may provide modularity whereby a series of sleeves may be provided having various dimensional properties. In one example, a solid metal area 154 may be defined on the sleeve 140 defining a passage 156. In this way, sutures or other attachment device may be inserted through the passage 156.

Figures 15, 16, 17:
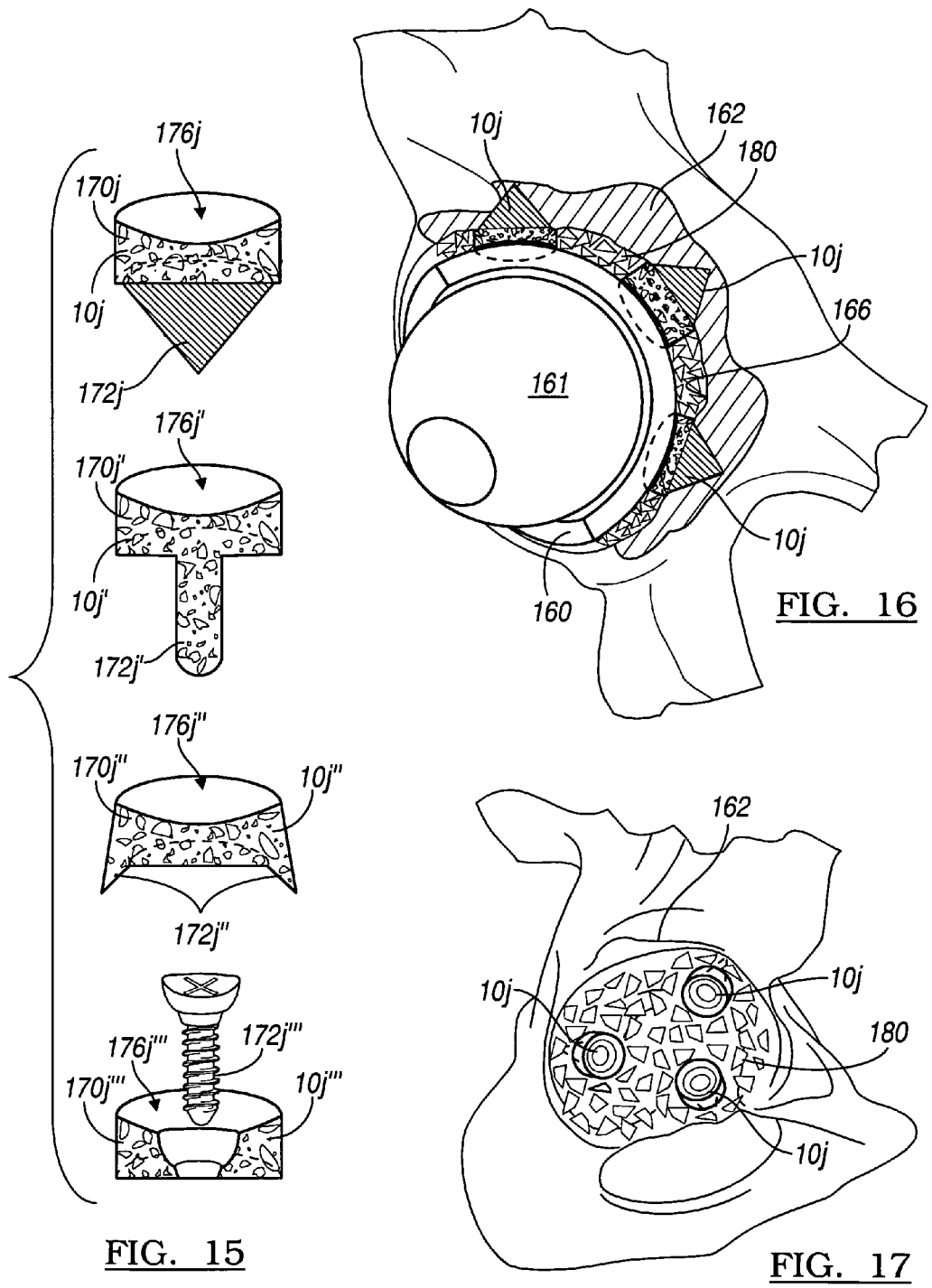
FIG. 15 is a perspective view of a series of augments according to the present teachings.
FIG. 16 is a perspective view of an exemplary acetabular cup implanted at an acetabulum built up with augments of FIG. 15.
FIG. 17 is a posterior lateral view of an acetabulum having a series of augments implanted therein.

Turning now to FIGS. 15-17, other porous metal augments and methods of utilizing the porous metal augments will be described. The porous metal augments 10*j*, 10*j*′, 10*j*″ and 10*j*′″ may be adapted for use with an acetabular cup 160 and femoral ball 161. In the example shown, the augments 10*j*, 10*j*″, 10*j*″ and 10*j*′″ in the form of spacers. The augments 10*j*, 10*j*′, 10*j*″ and 10*j*′″ may be implanted into an acetabulum 162 such as to build up an acetabular socket 166 that may have become sunken in. As used herein, the phrase sunken in is used to denote an acetabular socket that defines an imperfect concave surface. For example, an acetabular socket may define a greater radius at one area relative to another area. In the example shown in FIG. 16, the acetabular socket 166 defines a greater radius at its apex.

The augments 10*j*, 10*j*′, 10*j*″ and 10*j*′″ may define various heights for accounting for various defects. In general it may be desirable to create a substantially hemispherical landing area for an acetabular cup. As a result, an acetabular cup having a generally uniform thickness across its hemisphere may be used rather than a cup having a thicker apex region.

As shown, the augments 10*j*, 10*j*′, 10*j*″ and 10*j*′″ may comprise many shapes and sizes. In general, the augments 10*j*, 10*j*′, 10*j*″ and 10*j*′″ may include a body portion 170*j*, 170*j*″, 170*j*″ and 170*j*′″ and a piercing portion 172*j*, 172*j*′, 172*j*″ and 172′″. The body portion 170*j*, 170*j*″, 170*j*″ and 170*j*′″ may comprise porous metal such as described herein. The piercing portion 172*j*, 172*j*′, 172*j*″ may also comprise porous metal or alternatively comprise solid metal such as solid titanium. The body portion 170*j*, 170*j*″, 170*j*″ and 170*j*′″ may define a concave upper surface 176*j*, 176*j*′, 176*j*″ and 176′″ for accommodating an acetabular cup 160 thereon. In one example, bone chips (such as morselized bone) 180 may be used to fill an area around the augments 10*j*, 10*j*′, 10*j*″ and 10*j*′″. Of note, augment 10*j*′″ illustrates one example in which the piercing portion 172*j*′″ may be separately formed from the body portion 170*j*′″. The piercing portion 172′″ may comprise a bone screw.

Figure 18:
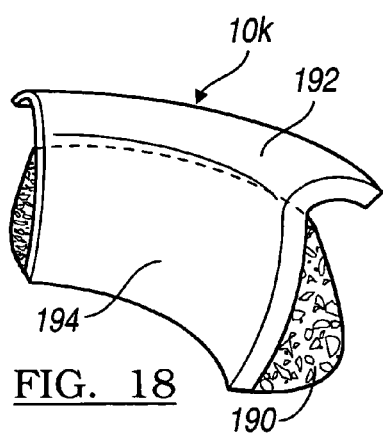
FIG. 18 is a perspective view of another augment according to the present teachings.
Figure 20:
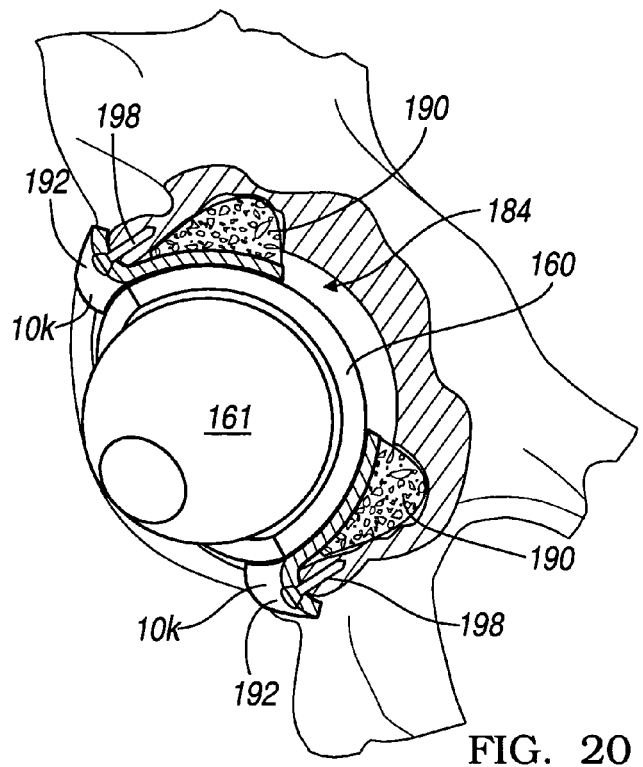
FIG. 20 is a perspective view of an exemplary acetabular cup implanted at an acetabulum built up with augments of FIG. 18 according to a second example.
Figure 19:
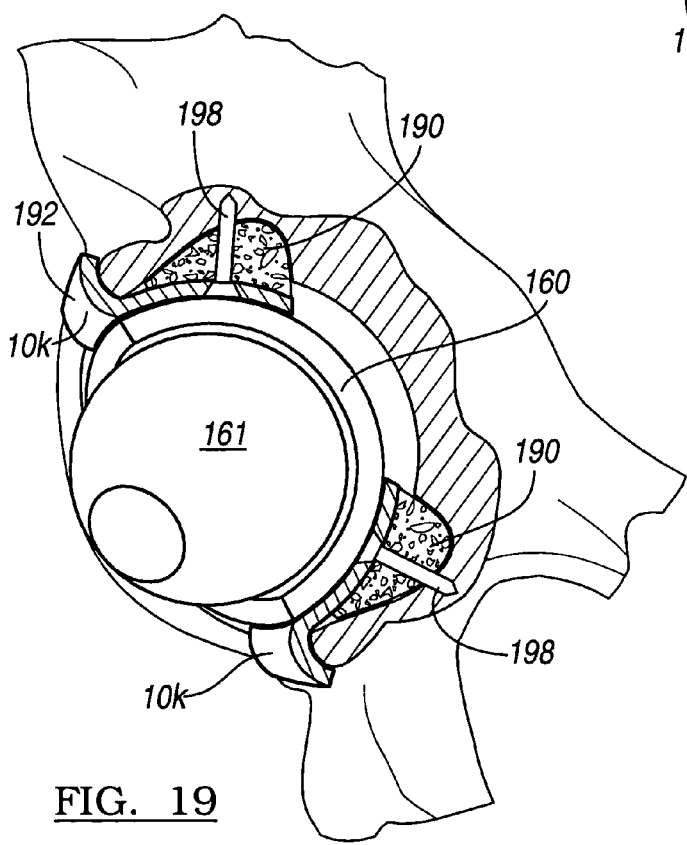
FIG. 19 is a perspective view of an exemplary acetabular cup implanted at an acetabulum built up with augments of FIG. 18 according to a first example.

With reference now to FIGS. 18-20, augments or spacers 10*k* according to additional features of the present teachings are shown. Again, the augments 10*k* may comprise various shapes and sizes. The augments 10*k* may be particularly useful for filling an annular space 184 around the acetabular cup 160. The augments 10*k* generally define a body portion 190 and a flange portion 192. The body portion 190 may comprise porous metal such as disclosed herein. The flange portion 192 may comprise solid metal such as titanium for example. In one example, the body portion 190 may be secured to the flange portion 192 through a sintering process. Other methods are contemplated. In general, a concave surface 194 is defined around an inboard portion of the flange 192.

In the example shown, the augments 10*k* may be secured to surrounding bone at a rim region of the acetabulum by advancing a fastener 198 such as a bone screw through a passage defined through the flange 192 (FIG. 20). In this way, the augments 10*k* may be secured at the solid metal portion instead of the porous metal portion. It is appreciated however that the augments 10*k* may alternatively or additionally be secured to the surrounding bone at the porous metal body portion. In this regard, fasteners 198 may be advanced through passages defined through the flange 192 and body portion 190 (FIG. 19). While not specifically shown, filler, such as morselized bone may be disposed in the space between the acetabular cup 160 and acetabular socket not occupied by the augments 10*k* similar to shown in FIGS. 16 and 17.

With reference now to FIGS. 21-23, augments or spacers 10*m* according to additional features of the present teachings are shown. The augments 10*m* may be particularly useful for filling an annular space around the acetabular cup 160. The augments 10*k* generally define a body portion 202 and at least one flange portion 206. The body portion 202 may comprise porous metal such as disclosed herein. The flange portion 206 may comprise solid metal such as titanium for example. In one example, the body portion 202 may be secured to the flange portion 206 through a sintering process. Other methods are contemplated.

In the example shown, the augments 10*m* may be secured into the acetabulum 162 by advancing a fastener such as a bone screw 198 through passages 200 defined through the flange 206. In this way, the augments 10*m* may be secured at the solid metal portion instead of the porous metal portion. It is appreciated however that the augments 10*m* may alternatively or additionally be secured to the surrounding bone at the porous metal body portion. In this regard, fasteners may be advanced through passages defined through the body portion 202. The augments 10*m* may be implanted into an acetabulum 162 such as to build up an acetabular socket 166 that may have become sunken in.

Figure 24:
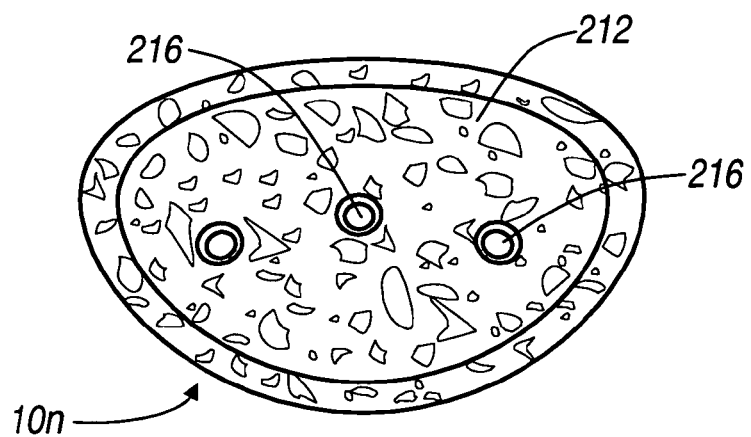
FIG. 24 is a perspective view of another augment according to the present teachings.
Figure 25:
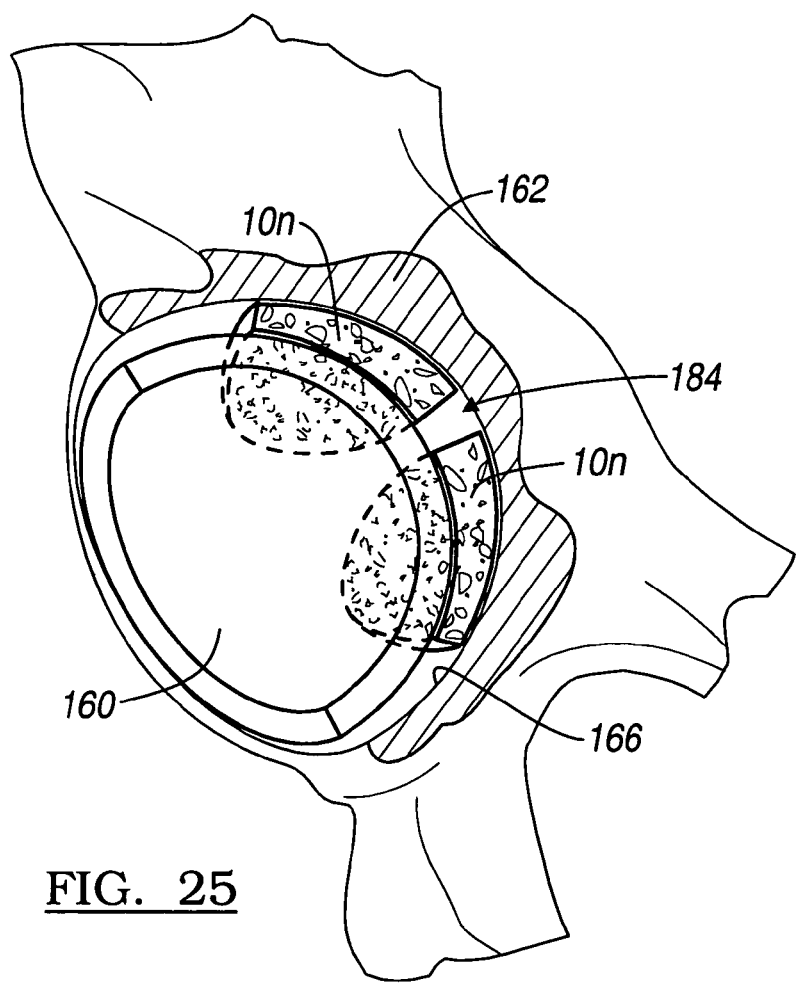
FIG. 25 is a perspective view of an exemplary acetabular cup implanted at an acetabulum built up with augments of FIG. 24 according to a first example.

Turning now to FIGS. 24 and 25, another porous metal augment 10*n* and method of utilizing a porous metal augment will be described. The porous metal augment 10*n* may be adapted for use with an acetabular cup 160. In the example shown, the augments 10*n* are in the form of spacers. The augments 10*n* may be implanted into an acetabulum 162 such as to build up an acetabular socket 166 that may have become sunken in. The augments 10*n* may define various heights for accounting for various defects. As described above, it may be desirable to create a substantially hemispherical landing area for an acetabular cup 160. As a result, an acetabular cup 160 having a generally uniform thickness across its hemisphere may be used rather than a cup having a thicker apex region.

The augment 10*n* generally defines a body portion 212 defining a truncated hemispherical cup. The augment 10*n* may be implanted alone or in combination with other augments 10*n* such as shown in FIG. 25. One or more passages 216 may be formed in the augments 10*n* for receiving fasteners during implantation. The augments 10*n* may alternatively or additionally be secured by bone cement and/or press fit. The acetabular cup 160 may then be implanted such as by way of fasteners and/or bone cement. Once the acetabular cup 160 is implanted, the augments 10*n* are further captured in a secure position relative to the acetabulum 162.

Figure 26:
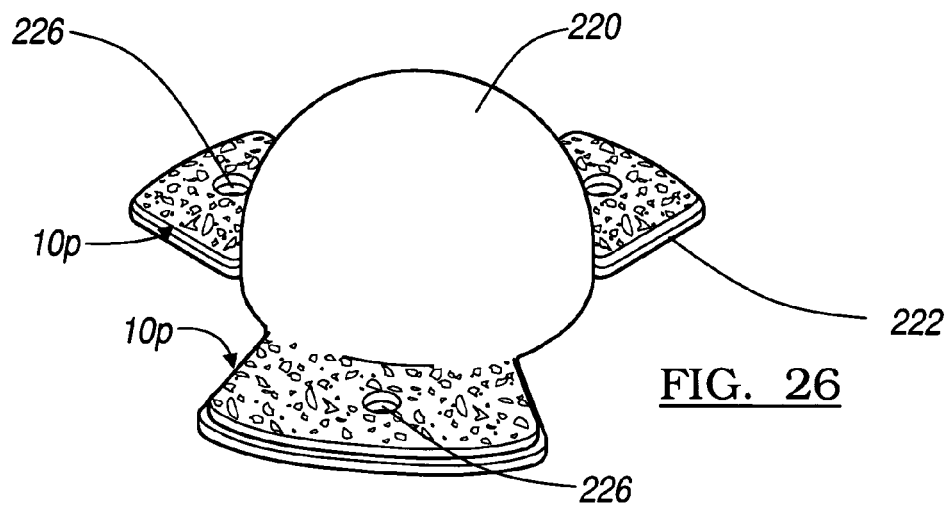
FIG. 26 is a perspective view of another augment according to the present teachings.
Figure 27:
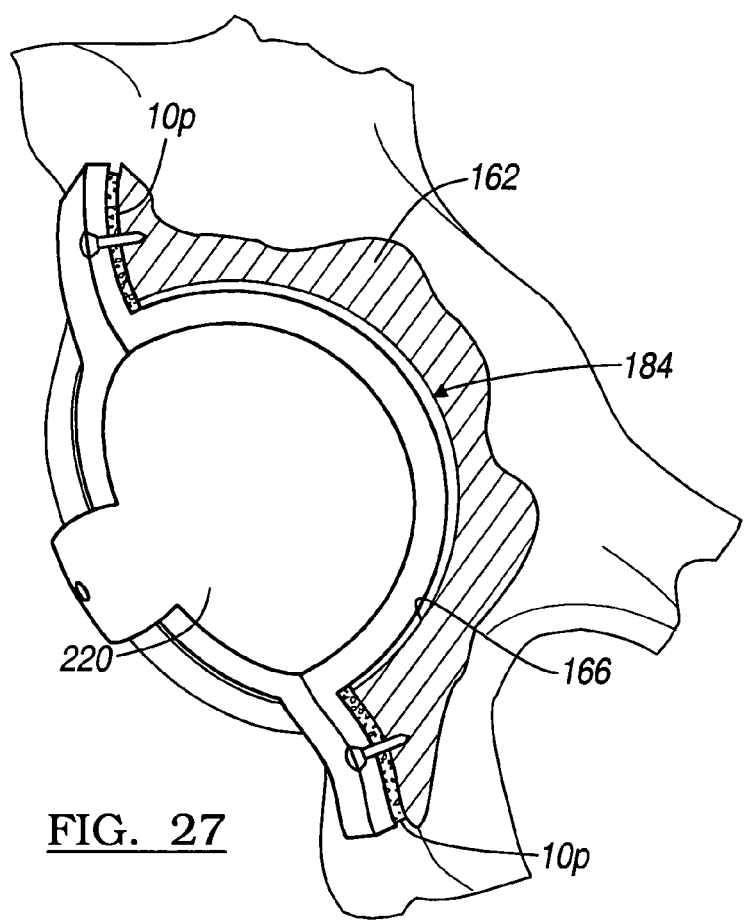
FIG. 27 is a perspective view of an exemplary acetabular cup implanted at an acetabulum utilizing the augments of FIG. 27 according to a first example.

Turning now to FIGS. 26 and 27, another porous metal augment 10*p* and method of utilizing a porous metal augment will be described. The porous metal augment 10*p* may be adapted for use with an acetabular cup 220. The acetabular cup 220 may define flanges 222 extending therefrom. In the example shown, the augments 10*p* are in the form of spacers and may be adapted to be attached to an underside of the flanges 222. Once attached to the flanges 222, the porous metal augments 10*p* may be implanted such that they oppose the surrounding bone surface of the acetabulum 162. The augments 10*p* may define various heights. Various methods may be used to attach the augments 10*p* to the acetabular cup 220. In one example, the augments 10*p* may be mechanically fastened to a solid titanium flange 222 such as through apertures 226. Alternatively the augments 10p may be sintered or press-fit to the flanges 222. In another example, the augments 10p may be reduced in size by way of a thermal treatment and subsequently press-fit onto the flanges 222.

Turning now to FIGS. 28-30, another porous metal augment 10q and method of utilizing a porous metal augment will be described. The porous metal augment 10q may be adapted for use with an acetabular cup 250. In one example, the acetabular cup 250 may be substantially similar to an acetabular cup as disclosed in commonly owned U.S. Pat. No. 6,458,161, which is incorporated herein by reference. In the example shown, the augments 10q are formed of porous metal such as discussed herein. The augments 10q may be adapted to be received at an underside of an attachment member or flange 252 of the acetabular cup 250. In one example, the flange 252 may be integrally formed with the acetabular cup 250. According to one example, the augment 10q may nest within a receptacle formed on the flange 252. In one example, the augment 10q may be secured by way of a fastener 258 extending through passages 256 formed on the augment 10q. According to another example, the augment 10q' may be retained by walls 260 defined on flange 252' in a clearance fit. In one example, the walls 260 may at least partially overlap the augment 10q'. In this way, the augment 10q' may be press-fit into an installed position at the receptacle. The augments 10q and 10q' may be adapted to encourage bone ingrowth thereat.

With specific reference to FIG. 30, augments 10r are shown suitably attached on acetabular cup 270 to attachment members or flanges 272. In one example, the augments 10r may be suitably attached by way of fasteners 278 passing through respective passages 276 formed in the augments 10r and flanges 272. According to another example, the augments 10r' may be retained within a receptacle defined on a flange 272' such as in a clearance fit. The augments 10r and 10r' may be adapted to encourage bone ingrowth thereat.

It is appreciated that the augments 10j, 10k, 10m, 10n, 10p and 10q may be used in any combination to satisfy the requirements of a given patient. Each of the augments 10j, 10k, 10m, 10n, 10p and 10q may provide load bearing properties for the acetabular cup 160 at the acetabulum 162. According to additional features, anti-infective agents (i.e. antibiotics), osteoconductive agents (i.e. hydroxyapatite), autologous blood products activated by thrombin to induce clots (i.e. blood, platelet rich plasma, autologous stem cells derived from any location within the body), hydrogels, either alone or containing autologous or allogenic cells, peptides, or other biologically active ingredients that induce or aide bone formation (i.e. bone morphogenic proteins) may be added and/or infiltrated to the porous metal of the implants, augments, and/or bone screws disclosed herein. Further, the porous metal structures described herein may also act as a carrier for bulk allograft or demineralized bone matrix products. Other growth promoters can be added and/or infiltered to the porous material of the implants, augments, anchors and bone screws described herein to promote appropriate soft or hard tissue response, ingrowth or attachment.

With reference now to FIGS. 15-25 an exemplary method for implanting porous metal augments and an acetabular cup according to the present teachings will be described in greater detail. At the outset, the size of the acetabular socket 166 may be determined. As described above, one advantage of the instant disclosure is that a surgeon may implant an acetabular cup having a uniform thickness. In this way, use of acetabular cups defining varying thickness, such as having a thicker cross-section at its apex, may be avoided. Instead, a surgeon may select various spacers, such as augments 10j, 10k, 10m and 10n disclosed herein (in any combination) to build up the acetabulum 162 and provide a substantially uniform radius support surface for accepting the acetabular cup 160. In this way, once the spacing between the acetabular cup 160 and the acetabular socket 166 is determined, spacers suitable to bridge the spacing between the acetabular cup and the acetabular socket may be selected. The augments 10j, 10k, 10m and 10n may then be implanted as described above. Once the augments 10j, 10k, 10m and 10n have been suitably implanted, the acetabular cup 160 may be implanted onto the collective support surface of the augments 10j, 10k, 10m and 10n such as by fasteners and/or bone cement. While not specifically shown, if fasteners are used, the fasteners may be adapted to pass through openings formed in the acetabular cup 160 and directly into the acetabulum 162, or additionally pass through the augments 10j, 10k, 10m and 10n.

While the invention has been described in the specification and illustrated in the drawings with reference to various embodiments, it will be understood by those skilled in the art that various changes may be made and equivalents may be substituted for elements thereof without departing from the scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. An acetabular cup assembly implantable at an acetabular socket, the acetabular cup assembly comprising:
    an acetabular cup having a partially spherical outer bone engaging surface, an opposite inner concave surface, and having a uniform thickness;
    a bearing liner having a partially spherical outer surface adapted to engage the inner concave surface of the acetabular cup;
    at least three spacers, each of said at least three spacers having a piercing portion and a body portion, said body portion formed of porous metal and including a radial support surface, said porous metal adapted to receive bone ingrowth through interstitial space at pores defined therein, said radial support surface including a concave acetabular cup supporting surface that engage and support said outer bone engaging surface of said acetabular cup, each of said at least three spacers further comprising a piercing portion extending from said radial support surface and adapted to be advanced into the acetabular socket, said at least three spacers having distinct heights in an implanted position, said distinct heights measured from said respective body portions to said corresponding piercing portions wherein each of said at least three spacers is separate from and independently movable relative to said acetabular cup and do not extend through said outer bone engaging surface of said acetabular cup, each of said at least three spacers configured to be selectively located at a desired position around the acetabular socket and adapted to collectively create a substantially hemispherical landing area that engages and supports said outer bone engaging surface of said acetabular cup to bridge a gap between the acetabular socket and said acetabular cup in said implanted position; and filler disposed between said acetabular cup and the acetabular socket in areas adjacent to said at least three spacers such that said at least three spacers and said filler collectively provide a continuous support surface adapted to support said acetabular cup at said bone engaging surface.

2. The acetabular cup assembly of claim 1 wherein said height is provided by said body portion in said implanted position.

3. The acetabular cup assembly of claim 2 wherein said piercing portion is formed of solid metal.

4. The acetabular cup assembly of claim 3 wherein said piercing portion is separately formed from said body portion.

5. The acetabular cup assembly of claim 4 wherein said piercing portion comprises a bone screw.

6. The acetabular cup assembly of claim 1 wherein said filler includes morselized bone.

7. The acetabular cup assembly of claim 1 wherein each of said at least three spacers is implanted at an apex region of the acetabulum.

8. The acetabular cup assembly of claim 1 wherein said piercing portion is integrally formed with said body portion and comprises a pair of piercing portions arranged at a perimeter of said body portion.

9. The acetabular cup assembly of claim 1 wherein said at least three spacers are adapted to be arranged radially around the acetabular socket.

10. An acetabular cup assembly implantable at an acetabular socket having an apex region and a rim region, the acetabular cup assembly comprising:

an acetabular cup having a partially spherical outer bone engaging surface, an opposite inner concave surface, and having a uniform thickness;

a bearing liner having a partially spherical outer surface adapted to engage the inner concave surface of the acetabular cup;

at least a first, a second, and a third spacer independently movable relative to each other and said acetabular cup, said first spacer having a first body portion that includes a first concave support surface that engage and support said outer bone engaging surface of said acetabular cup, said second spacer having a second body portion that includes a second concave support surface that engage and support said outer bone engaging surface of said acetabular cup, said third spacer having a third body portion that includes a third concave support surface that engage and support said outer bone engaging surface of said acetabular cup, said first, second, and third spacers being formed of porous metal and both further comprising a piercing portion extending from said concave support surface and adapted to be advanced into the acetabular socket, said first and second spacers having distinct heights measured between respective piercing portions and body portions in an implanted position and that are adapted to collectively create a substantially hemispherical landing area that engages and supports said outer bone surface of said acetabular cup to bridge a gap formed between the acetabular socket and said acetabular cup; and a filler disposed between said aeetabular cup and the acetabular socket in areas adjacent to said spacers such that said spacers and said filler collectively provide a continuous support surface that is adapted to support said acetabular cup at said bone engaging surface;

wherein said first, second, and third spacers are separate from and independently movable relative to each other and said acetabular cup, and are adapted to be independently advanced into the acetabular socket at respective locations between the apex region and the rim region of the acetabular socket, and wherein said first, second, and third spacers do not extend through said outer bone engaging surface of the acetabular cup.

11. The acetabular cup assembly of claim 10 wherein said distinct heights are provided by said first and second body portions in said implanted position.

12. The acetabular cup assembly of claim 11 wherein said piercing portion is formed of solid metal.

13. The acetabular cup assembly of claim 12 wherein said piercing portion is separately formed from said body portion.

14. The acetabular cup assembly of claim 13 wherein said piercing portion comprises a bone screw.

15. The acetabular cup assembly of claim 14 wherein said body portion defines a passage and a countersink cavity, and wherein said bone screw has a shank portion that extends at least partially through said passage and a head portion that nests in said countersink cavity in said implanted position.

16. The acetabular cup assembly of claim 15 wherein said head portion of said bone screw is concave.

17. The acetabular cup assembly of claim 10 wherein said filler includes morselized bone.

18. The acetabular cup assembly of claim 10 wherein said piercing portion is integrally formed with said respective body portion and comprises a pair of piercing portions arranged at a perimeter of said respective body portion.

19. The acetabular cup assembly of claim 18 wherein said piercing portion comprises a longitudinal portion having a constant outer diameter that terminates at a distal tip portion having an arcuate terminal end.

20. An acetabular cup assembly implantable at an acetabular socket, the acetabular cup assembly comprising:

an acetabular cup having a partially spherical outer bone engaging surface, an opposite inner concave surface, and having a uniform thickness;

a bearing liner having a partially spherical outer surface adapted to engage the inner concave surface of the acetabular cup;

a first spacer having a first body portion extending a first height from a first piercing portion, said first body portion having a first concave acetabular cup supporting surface that engage and support said outer bone engaging surface of said acetabular cup;

a second spacer having a second body portion extending a second height from a second piercing portion, said second body portion having a second concave acetabular cup supporting surface that engage and support said outer bone engaging surface of said acetabular cup;

a third spacer having a third body portion extending a third height from a third piercing portion, said third body portion having a third concave acetabular cup supporting surface that engage and support said outer bone engaging surface of said acetabular cup; and a filler that is configured to be disposed between said acetabular cup and the acetabular socket in areas adjacent to said first, second and third spacers, such that said first, second and third spacers and said filler collectively provide a continuous support surface that is adapted to support said acetabular cup at said bone engaging surface;

wherein said first, second and third spacers are separate from and independently movable relative to each other and said acetabular cup, said first height being distinct than at least one of said second and third heights, wherein said first, second and third piercing portions are adapted to be advanced into the acetabular socket at locations where said first, second and third heights cooperate to collectively create a substantially hemispherical landing area that engages and supports said outer bone engaging surface of said acetabular cup, and wherein said first, second, and third spacers do not extend through said outer bone engaging surface of the acetabular cup.

* * * * *

UNITED STATES PATENT AND TRADEMARK OFFICE
CERTIFICATE OF CORRECTION

PATENT NO. : 8,021,432 B2  
APPLICATION NO. : 11/546500  
DATED : September 20, 2011  
INVENTOR(S) : Jason D. Meridew et al.

Page 1 of 1

It is certified that error appears in the above-identified patent and that said Letters Patent is hereby corrected as shown below:

In the Specifications:

Column 1, Line 9, "disclosures" should be --disclosure--.

Column 4, Line 31, "suture" should be --sutures--.

Column 7, Line 14, After "10j'"", insert --are--.

Column 7, Line 32, First occurrence of "170j'""" should be --170j'--.

Column 7, Line 33, "172'""" should be --172j'"--.

Column 7, Line 33, First occurrence of "170j'""" should be --170j'--.

Column 7, Line 37, First occurrence of "170j'""" should be --170j'--.

Column 7, Line 39, "176'""" should be --176j'"--.

Column 7, Line 44, "172'""" should be --172j'"--.

In the Claims:

Column 11, Line 62, Claim 10, After "bone", insert --engaging--.

Signed and Sealed this  
Twenty-eighth Day of May, 2013

Teresa Stanek Rea  
*Acting Director of the United States Patent and Trademark Office*